(12) United States Patent
Weber

(10) Patent No.: US 7,494,488 B2
(45) Date of Patent: *Feb. 24, 2009

(54) FACIAL TISSUE STRENGTHENING AND TIGHTENING DEVICE AND METHODS

(75) Inventor: Paul Joseph Weber, Fort Lauderdale, FL (US)

(73) Assignee: Pearl Technology Holdings, LLC, Palm Harbor, FL (US)

(*) Notice: Subject to any disclaimer, the term of this patent is extended or adjusted under 35 U.S.C. 154(b) by 676 days.

This patent is subject to a terminal disclaimer.

(21) Appl. No.: 10/903,325

(22) Filed: Jul. 30, 2004

(65) Prior Publication Data

US 2005/0055073 A1 Mar. 10, 2005

Related U.S. Application Data

(63) Continuation-in-part of application No. 09/749,497, filed on Dec. 22, 2000, now Pat. No. 6,974,450, which is a continuation-in-part of application No. 09/475,635, filed on Dec. 30, 1999, now Pat. No. 6,440,121, and a continuation-in-part of application No. 09/478,172, filed on Jan. 5, 2000, now Pat. No. 6,432,101, and a continuation-in-part of application No. 09/588,436, filed on Jun. 6, 2000, now Pat. No. 6,391,023, which is a continuation-in-part of application No. 09/085,948, filed on May 28, 1998, now Pat. No. 6,203,540.

(51) Int. Cl.
*A61B 18/18* (2006.01)
*A61B 18/14* (2006.01)

(52) U.S. Cl. .............. 606/2; 606/9; 606/13; 606/20; 606/27; 606/33; 606/41; 604/19

(58) Field of Classification Search ............. 606/2, 606/41
See application file for complete search history.

(56) References Cited

U.S. PATENT DOCUMENTS

| | | | | |
|---|---|---|---|---|
| 2,591,125 | A | * 4/1952 | Braun | 604/311 |
| 5,695,510 | A | 12/1997 | Hood | 606/169 |
| 5,755,753 | A | 5/1998 | Knowlton | 607/98 |
| 5,871,524 | A | 2/1999 | Knowlton | 607/101 |
| 5,873,855 | A | 2/1999 | Eggers | 604/114 |
| 5,919,219 | A | 7/1999 | Knowlton | 607/102 |
| 5,935,143 | A | 8/1999 | Hood | 606/169 |
| 5,948,011 | A | 9/1999 | Knowlton | 607/101 |
| 5,984,915 | A | 11/1999 | Loeb et al. | 606/9 |

(Continued)

OTHER PUBLICATIONS

P.J. Weber et al., Bulbous-Lysing Underminers, J. Dermatol Surg. Oncol., 15:12, Dec. 1989, pp. 1252-1253.

*Primary Examiner*—Lee S Cohen
(74) *Attorney, Agent, or Firm*—Matthew D. Thayne; Stoel Rives LLP

(57) ABSTRACT

A device is described that can be used quickly and accurately by surgeons to provide uniform facial tissue planes that are tunnel-free and wall-free thus optimizing face lifting, tightening, and implant delivery. The device is comprised of a shaft with a substantially planar tip further comprised of relative protrusions and energized relative recession lysing segments. Forward motion of the device precisely divides and energizes various tissue planes causing contraction, especially via the fibrous tissues. Other forms of energy and matter can be delivered down the shaft to further enhance desirable tissue modification and contraction.

40 Claims, 17 Drawing Sheets

U.S. PATENT DOCUMENTS

| | | | |
|---|---|---|---|
| 6,033,398 A * | 3/2000 | Farley et al. | 606/27 |
| 6,176,854 B1 | 1/2001 | Cone | 606/15 |
| 6,241,753 B1 | 6/2001 | Knowlton | 607/99 |
| 6,264,652 B1 | 7/2001 | Eggers et al. | 606/41 |
| 6,277,116 B1 | 8/2001 | Utely et al. | 606/42 |
| 6,311,090 B1 | 10/2001 | Knowlton | 607/101 |
| 6,350,276 B1 | 2/2002 | Knowlton | 607/104 |
| 6,377,854 B1 | 4/2002 | Knowlton | 607/101 |
| 6,377,855 B1 | 4/2002 | Knowlton | 607/101 |
| 6,381,497 B1 | 4/2002 | Knowlton | 607/101 |
| 6,381,498 B1 | 4/2002 | Knowlton | 607/101 |
| 6,387,380 B1 | 5/2002 | Knowlton | 424/400 |
| 6,405,090 B1 | 6/2002 | Knowlton | 607/102 |
| 6,413,255 B1 | 7/2002 | Stern | 606/41 |
| 6,425,912 B1 | 7/2002 | Knowlton | 607/101 |
| 6,430,446 B1 | 8/2002 | Knowlton | 607/101 |
| 6,438,424 B1 | 8/2002 | Knowlton | 607/101 |
| 6,453,202 B1 | 9/2002 | Knowlton | 607/102 |
| 6,461,350 B1 | 10/2002 | Underwood | 606/32 |
| 6,461,354 B1 | 10/2002 | Olsen | 606/41 |
| 6,461,378 B1 | 10/2002 | Knowlton | 607/104 |
| 6,470,216 B1 | 10/2002 | Knowlton | 607/101 |
| 6,482,201 B1 | 11/2002 | Olsen | 606/41 |
| 6,514,248 B1 | 2/2003 | Eggers | 606/41 |
| 6,544,261 B2 | 4/2003 | Ellsberry | 606/41 |
| 6,557,559 B1 | 5/2003 | Eggers | 128/898 |
| 6,595,990 B1 | 7/2003 | Weinstein | 606/41 |
| 6,623,454 B1 | 9/2003 | Eggers | 604/114 |
| 6,632,193 B1 | 10/2003 | Davison | 604/22 |
| 6,632,220 B1 | 10/2003 | Eggers | 606/41 |
| 6,659,106 B1 | 12/2003 | Hovda | 128/898 |
| 6,719,754 B2 | 4/2004 | Underwood | 606/32 |
| 6,740,079 B1 | 5/2004 | Eggers | 606/34 |

* cited by examiner

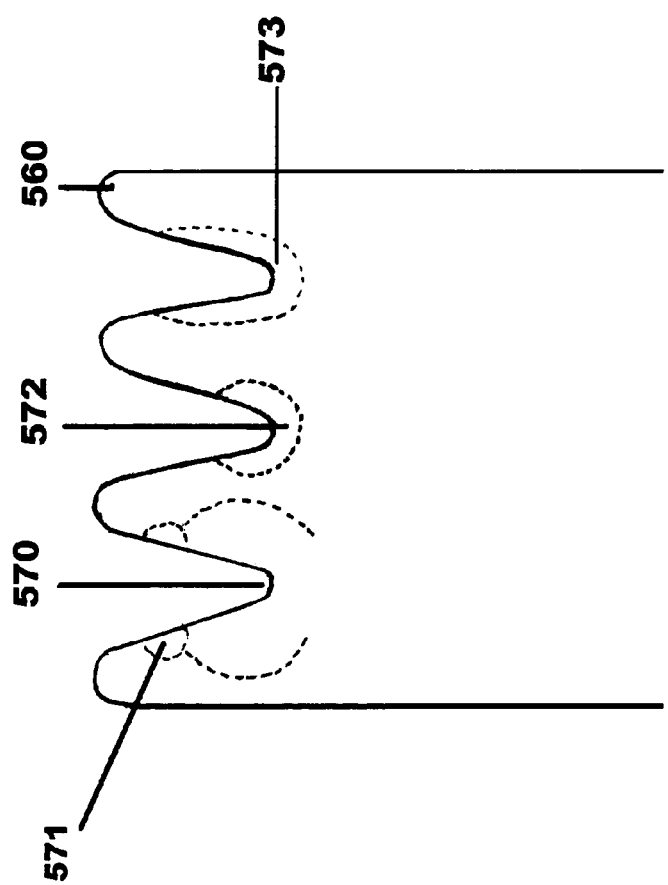

FACIAL TISSUE STRENGTHENING AND TIGHTENING DEVICE AND METHODS

This application is a continuation-in-part of U.S. patent application Ser. No. 09/749,497, titled "Face-Lifting Device" and filed Dec. 22, 2000, now U.S. Pat. No. 6,974,450, incorporated herein by reference; which is a continuation-in-part of U.S. patent application Ser. No. 09/475,635 titled "Surgical Device for Performing Face-Lifting Using Radiofrequency Energy" and filed Dec. 30, 1999, now U.S. Pat. No. 6,440,121, incorporated herein by reference; and is a continuation-in-part of U.S. patent application Ser. No. 09/478,172, titled "Surgical Device for Performing Face-Lifting Using Electromagnetic Radiation" and filed Jan. 5, 2000, now U.S. Pat. No. 6,432,101, incorporated herein by reference; and is a continuation-in-part of U.S. patent application Ser. No. 09/588,436, titled "Thermal Radiation Facelift Device" and filed Jun. 6, 2000, now U.S. Pat. No. 6,391,023, incorporated herein by reference; which is a continuation-in-part of U.S. patent application Ser. No. 09/085,948, titled "Ultrasound and Laser Face-Lift and Bulbous Lysing Device" and filed May 28, 1998, now U.S. Pat. No. 6,203,540.

BACKGROUND OF THE INVENTION

1. Field of the Invention

The invention relates to face-lifting devices. More specifically, however, this application and those co-pending perform face-lifting via precise uniform planar tissue separation with tissue tightening resulting from energetic alteration of the freshly divided tissue planes. The device acts below the surface of the skin through the most minimal of incisions. The invention is the only tip configuration able to generate over 1000 sqcm of wall-less undermined facial skin in under 20 minutes using only three 1 cm long incision. Although, the invention can dramatically and uniformly affect large subsurface areas and volumes of tissue, the device would be considered as minimally invasive cosmetic surgery since the clinically visible incisions are relatively small and recovery period relatively rapid. The invention also pertains to attendant methods for enhancing the energetic effects of the divided tissue planes via concurrent application of organic and inorganic, chemicals and materials. The goal of this application and related applications is to, with minimal invasion and complete epidermal avoidance, efficiently and uniformly separate and divide human tissue planes without leaving remnant fibrous tissue tunnels, to concomitantly coagulate distant unseen blood vessels, and to energetically alter tissues on either side of the said divided tissue planes thereby to induce tissue contraction and strengthening via collagen formation. Additionally, a unique and important side-benefit of the complete and efficient separation of human facial tissue planes (without leaving remnant fibrous tissue tunnels) is to interfere with the reformation of targeted wrinkles, undulations, folds or defects in the surface tissues of the face via undercutting their deep fibrous attachments.

2. Description of Related Art

Animal and human skin is usually composed of at least 3 layers. These layers include the: outermost surface epidermis which contains pigment cells and pores, the dermis or leather layer, and the subdermis which is usually fat, fibrous tissue or muscle. The current target of most rejuvenation methods' energies is the dermis which is comprised mostly of fibroblast cells. Fibroblasts produce a bed of collagen and ground substances such as hyaluronic acid for the dermis. When a disturbance occurs in the dermis such as trauma, fibroblasts are activated and not only produce new reparative strengthening collagen but contract, thus tightening and sealing healing tissue. Collagen is a basic structural protein found through almost all of the human body. It is present in under 5% of the epidermis, half of the dermis and about 20% of the subcutaneous depending upon the race, location, age and previous trauma of the individual. Immediate collagen shrinkage is usually parallel to the axis of the individual collagen fiber which roughly corresponds to the direction of collagenous strands as seen when stained and viewed microscopically. Thermal damage to collagen is likely brought about by hydrolysis of cross-linked collagen molecules and reformation of hydrogen bonds resulting in loss of portions or all of the characteristic collagen triple-helix. New collagen formed as the result of trauma and some diseases; new collagen is technically scar tissue. Nonetheless, a controlled and uniform formation of scar tissue can be medically beneficial and visually desirable as can be seen in cases of previously sun-damaged women's faces following a deep chemical peel. Thus, the formation of new collagen in a desirable, uniform and controlled fashion may lead to tissue strengthening as well as tightening. "... In the human face, without uniformity there is only deformity."

Currently, a need exists for a surgical device with the following assets: 1) minimally invasive insertion—to treat the entire face and neck through only three ⅜ of an inch incisions, 2a) precise horizontal/tangential tissue layer separation without leaving remnant fibrous (collagenous) tissue tunnels, yet preserving nerve and vessel layered networks while maintaining straight horizontal tracking to break any and all fibrous bonds holding the dermis to deeper structures [seen on the surface as visible wrinkles, folds, crevices], 2b) cutting tip energy application—to coagulate blood vessels located too far from the minimal incisions to be visible the naked eye since use of endoscopes is cumbersome and time-consuming, 3) direct subsurface tissue energy application capability to alter, induce or stimulate fibroblasts/collagen resulting in skin tightening and strengthening thus completely bypassing the ultra-sensitive and fragile epidermis and thus avoiding visible surface scaring and pigment loss/excess.

Applicant meets the following needs: 1) minimally invasive surgery with very few visible surgical device entrance wounds, 2) rapid patient recovery and healing, 3) ability to be used with tumescent anesthesia, 4) complete epidermal avoidance or bypass, 5) 20 minute operating time in the face and neck to efficiently separate and divide human tissue planes, while coagulating blood vessels, 6) concurrent ability to alter tissues adjacent to the divided tissue planes thereby inducing collagenous reformation, contraction and strengthening, 7) complete breaking and detachment of all of the fibrous binding elements between the dermis and the deeper skin structures so that reformation and reattachment will not occur thus reducing the chance that targeted wrinkles, undulations, folds or defects in the surface tissues of the face will reappear following the contractile healing phase. Currently no device or method in the medical literature addresses all of these concerns simultaneously. After the insertion of simple tumescent anesthesia, a human facial procedure is estimated to take only 15 minutes to perform in experienced hands, including stitching.

Cutting (in surgery), lysis (in surgery), sharp undermining and blunt undermining have been defined in applicant's prior related art. Sharp instrument undermining is a mainstay of plastic surgery, however even experienced plastic surgeons performing face-lifts may, from time to time, "lose" the correct tissue plane while performing sharp undermining; even with great skill and experience, previous surgical scarring or aberrant anatomy may thwart surgical perfection during sharp scissor or scalpel tissue dissection/undermining. Blunt undermining employs a rounded, non-sharp tipped, instrument or even human finger to find the path of least resistance between tissues; once the desired plane is found by the surgeon, blunt dissection offers the benefit of a reduced chance to traumatize or damage vital structures such as facial blood vessels or nerves (to facial muscles) thereby reducing the chances for bleeding or permanent facial paralysis. Unfortunately, blunt undermining alone between highly fibrous tissues that exists in the human face results in irregular tunnels with thick fibrous walls.

Disadvantages of the current face-rejuvenating techniques using LASERS are described in the aforementioned referenced patents and those of applicant. Current face-lifting instruments that cut with other than manual energy are incapable of providing a uniform wall free tissue plane during energized face-lifting dissection. Current lasers must be crudely fired from positions outside the patient to energize tissue within the face and cut in a very imprecise fashion (See "Manual of Tumescent Liposculpture and Laser Cosmetic Surgery" by Cook, R. C. and Cook, K. K., Lippincott, Williams, and Wilkins, Philadelphia ISBN: 0-7817-1987-9, 1999) using current energy assisted face-lifting methods. Currently deep dermal tissue is treated, altered or damaged with little precision. Complications from the aforementioned technique have been summarized by Jacobs et al. in Dermatologic Surgery 26: 625-632, 2000.

Disadvantages of the current face-lifting techniques using electrosurgical devices have been defined in the referenced patents and those of applicant.

The paper-thin layer of the skin that gives all humans their pigmentary color and texture is the epidermis. Unfortunately, virtually every skin rejuvenation system that has existed until now (with the exception of injectable skin filling compounds) and even traditional face-lifting surgery (when cutting through the skin around the ear is considered) must pass through the epidermis to attempt to reach and treat the dermis. Damage to the epidermis and its component structures often results in undesirable colorations or color losses to the skin as is seen in scarring. The prime consideration over the last decade for scientists and engineers regarding skin rejuvenation procedures is how to spare damage to the thin but critical epidermis and adjoining upper dermal layer.

This patent application will serve as the first submitted report that significant trauma to a tissue plane adjacent the dermis such, as the subcutaneous (fatty) layer, can induce the opposing overlying layer of dermis to contract, presumably due to inflammatory mediators or cells crossing between the planes. Additionally, the orderly and precise formation of new collagen (neocollagenesis) in the dermis by the invention and related patents may lead to desirable tissue strengthening as well as tightening. As the human facial skin ages, some of the strongest layers of tissue which plastic surgeons use to stitch-tighten the face, the fibrous layers known as fascia or SMAS=Superficial Musculo Aponeurotic System, become thinner and weaker. Disease and environmental factors such as diet and chemical exposure also take their toll. Various embodiments of the invention can be passed along these layers activating fibroblasts, increasing the amount of collagen as a result of the precisely delivered traumatic or tissue-altering energies the device inflicts to the uniform tissue planes the device creates, thus thickening and strengthening the aging layers. If even further strengthening is needed in the giant, precise, bloodless subsurface plane that the device establishes using only three minimally invasive 1 cm incisions, then three minimal incisions allow for the introduction into the face of reinforcing meshes, tethers, slings made of organic and/or inorganic materials as well as facial implants. Prolotherapy agents have never been previously described for facial tightening or strengthening, to our knowledge, possibly because there is currently no instrument available to precisely create uniform facial tissue planes upon which the chemical gradients' of potential prolotherapy agents can act. Following applicants uniform invention-induced facial tissue plane formations, prolotherapy fluids can be injected into the minimal incisions to enhance the actions of the instant device or to cause their own primary effect.

Externally applied Fractional Photothermolysis is distinguishable from this invention and related art. Fractional Photothermolysis (FP) is well described in a most recent publication by Rox Anderson: "Fractional Photothermolysis: A New Concept for Cutaneous Remodeling Using Microscopic Patterns of Thermal Injury" published in Lasers in Surgery and Medicine, volume 34, pages 424-438, 2004 by Manstein D, Herron S, Tanner H, and Anderson R. Anderson states "There is an increasing demand for an effective and safe laser treatment that repairs photo-aged skin. Two treatment modalities, ablative skin resurfacing (ASR), and non-ablative dermal remodeling (NDR), have been developed to address this demand. All currently available laser treatments, however, exhibit significant problems and these laser systems typically operate safely and effectively only over a narrow, patient dependent treatment range." The prime reason for the narrow range is the ultra-delicate epidermis. Anderson advocates, "Studies indicate that the efficacy for treatment of rhytides (wrinkles) and solar elastosis improves with increased thermal damage depth [Anderson's reference 9]. The most effective Erbium:YAG (Yttrium Aluminum Garnet) lasers for the treatment of rhytides use longer pulse durations to increase the residual thermal damage depth [ref 10]. To enhance wound healing without sacrificing efficacy, a combined approach has become popular for ASR [ref 11]. To overcome the problems associated with ASR procedures, the so-called NDR technologies have emerged that selectively damage the dermal tissue to induce a wound response, but avoid damage to the epidermis [refs 12-25]. In this technique, controlled dermal heating without epidermal damage is achieved by combination of laser treatment with properly timed superficial skin cooling. The wound response to thermally damaged dermal tissue results in formation of new dermal collagen and repair of tissue defects related to photo-aging. The absence of epidermal damage in NDR techniques significantly decrease the severity and duration of treatment related side effects. Lasers used for NDR procedures have a much deeper optical penetration depth that superficially absorbed ablative Erbium:YAG and CO2 lasers. While it has been demonstrated that these techniques can avoid epidermal damage, the major drawback of these techniques is limited efficacy [ref 26]. Anderson measures and reports a mere 2% tissue shrinkage results: " . . . small but reproducible, skin shrinkage was observed as measured by microtattoo placement. Skin shrinkage was still evident 3 months following treatment . . . " Anderson's concern to minimize permanent epidermal damage, especially in darker-skinned patients, is evident "In our study, there were several dark-skinned subjects, who demonstrated little or no significant pigmentation abnormalities after FP at low or medium MTZ (Microscopic Treatment Zones) densities per treatment. Histology revealed that there is a localized, well-controlled melanin release and transport mechanism using MENDs (Micro Epidermal Necrotic Debris) as a 'vehicle'."

Externally applied FP as described by Anderson differs from applicant. Anderson's FP device must be placed on the external skin surface and has not been described for internal use to reach the outer layers of skin from the inside route. Anderson's FP device is external, not designed to, not can it, break the fibrous tissues beneath the surface skin and cannot be passed beneath the skin without another attachment or device such as applicant's tip to "ice-break" the way. Without breaking the fibrous bonds below the skin surface that attach the surface skin to the deeper structures of the face that bind wrinkles in permanently. Unfortunately, surface treatments are only temporary and cause only minor tightening. Anderson's externally applied art must restrict energy delivery which renders only a 2% tightening in order to avoid damaging the fragile epidermis. Anderson uses MENDs (Micro Epidermal Necrotic Debris) that allow sufficient time and space for traumatic epidermal re-growth to occur to avoid permanently damaging the epidermis. An embodiment of applicant creates MEND or even Focal Macroscopic Necrosis (FMN) and delivers energy, from inside out on uniform tissue planes allowing uniform energy gradients and therefore bypass the delicate and sensitive epidermis while still bringing about deeper tissue contraction. Applicant's U.S. Pat. No. 6,203,540 involves laser fiberoptics which can be pulsed and delivered below the skin to bring about FMN like lesions. Fiber sizes mentioned would provide energy destruction patterns greater in size then MEND's; however, fiberoptic size in U.S. Pat. No. 6,203,540 may be reduced to bring about damage volumes somewhat greater than or approaching the size of MENDs and discharge more energy 'upward' toward the epidermis than Anderson for greater dermal alteration with minimized epidermal effect. Applicant allows for the treatment of a larger surface area much more rapidly because of the capability for greater direct, internal energy transfer. Applicant treats the entire face and neck to the collarbones in under 20 minutes operating time by an experienced hand. Anderson's device delivers only a 2% tissue contraction measurement in tissue under no growing tension as compared with applicant's 20%-30% contraction in 10×10 sqcm tattoo grids on the abdomens of baby pigs that doubled in size over the 3 month study period (unpublished, photographs available upon request). The difference in results is largely due to the great disparity between the two methods in energy delivered to the tissues. (Underlining was added for emphasis).

Laser treated tissues and electrosurgically treated tissues are similar in several respects. However most importantly, when it comes to internally electro-modifying human tissues, is that immediately local vaporized tissue regions take on a relatively high electrical impedance, and increase the voltage difference, thus altering further local electrical penetration/treatment of the tissues. Irregular energy absorption by irregularly thick and irregularly formed fibrous tunnel remnants resulting from the use of devices, other than applicant's, would thus cause visible irregular skin surface effects on healing. Other reasons why applying tissue-altering energy to precisely formed facial tissue planes without fibrous tunnel wall remnants is important include: "the electrical impedance of tissue is known to decrease with increasing frequency due to the electrical properties of cell membranes which surround the electrically conductive cellular fluids. As a result of higher tissue impedance, the current flux lines tend to penetrate less deeply resulting in a smaller depth of tissue heating. If greater depths of issue heating are to be effected a higher output voltage and frequency must be used. Lower impedance paths will automatically result in lower resistive heating since heating is proportional to the operating current squared multiplied by impedance."

Monopolar electrosurgical instruments possess a single active electrode at the tip of an electrosurgical probe. Low voltage applied to the active electrode in contact with the target tissue moves electrical current through the tissue and the patient to a dispersive grounding plate or an indifferent electrode. Voltage differences between the active electrode and the target issue cause an electrical arc to form across the physical gap between the electrode and tissue. At the point of arc contact with tissue, rapid tissue heating occurs due to high current density between the electrode and tissue. Current density causes cellular fluids to vaporize into steam yielding a cutting effect. Monopolar electrosurgery methods generally direct electric current along a defined path from the active instrument electrode through the patient's body into the return or grounding electrode. Small diameter electrodes increase electrical field intensity in the locality. Bipolar configurations more easily control the flow of current around the active region of a treatment device which reduces thermal injury and thus minimizes tissue necrosis and collateral tissue damage while reducing conduction of current through the patient. Applicant believes that the optimum combination of electrical energies to be used in conjunction with a protective tip is monopolar cutting current in the lysing segments and adjunctive monopolar or bipolar coagulation current along the planar aspects of the device. Because of applicant's discovery that the highly resistive lower fatty layer plane of facial dissection may be electrically or energetically traumatized and eventually result in the transfer of mediators into overlying, over-draping dermis causing its contraction (likely by inflammatory chemical mediators or cellular transfer), logically higher energy formats than bipolar would be necessary to necrose the fatty layer for the transfer effect (subcutaneous to dermis traumatic inflammatory shrinkage transfer effect=SDTISTE) to occur.

Eggers in U.S. Pat. No. 5,871,469 and related patents differs from applicant. Eggers teaches an electrosurgical device that requires an ionic fluid to create conduction between minute arrayed electrodes and relies on an ionic fluid source from within the instrument to function optimally. Eggers teaches bipolar energy flows principally between pairs or groups of minute electrodes arranged in various arrays depending upon the embodiment chosen. Unfortunately, observing Eggers' diagram 2c top view may lend the incorrect impression of similarity in shape to the applicant tips; however, in Eggers the protrusions are electrodes/conductors which would irregularly violate and destroy the vital human facial tissue structures including the subdermal plexus of vessels on passage if creation of a plane were attempted or even possible. Applicant's protrusions are non-conductive or insulated protectors and facilitate precise device movement, wall-free uniform tissue plane formation while providing for vital subdermal plexus tissue preservation. Eggers' embodiment of electrode arrays at the tip may be likened to component rasps of a oil well drill bit where the array protrusions bite into and chew away to form a canal in the target tissue, a desired effect that is totally counter to the intentions and dynamics of applicant. To quote Eggers in U.S. Pat. No. 5,871,469 column 4 line 49: "The electric field vaporizes the electrically conductive liquid into a thin layer over at least a portion of the active electrode surface and then ionizes the vapor layer . . . ". Eggers teaches vaporizing a thin layer of an optimizing conducting fluid; additional application of a conducting fluid is not a necessity for applicant. Eggers furthermore reveals in column 11: "The depth of necrosis (tissue death, lethal alteration) will typically be between 0 to 400 microns and usually 10 to 200 microns (=0.2 mm)." The energy levels that are generated by applicant allows tissue damage to depths of 4 mm (4,000 microns) over twenty times greater than Eggers' safe range. Only applicant can create tunnel free, wall free, uniform tissue planes upon which to apply tissue modifying energy or tissue modifying chemicals and render uniform gradient potential. Eggers' U.S. Pat. No. 5,871,469 external skin resurfacing (Visage®) requires an external ionic fluid drip and has been in clinics and is known not to remove much more than very fine wrinkles without epidermal pigment changes or scarring. Only the thinnest wrinkles can be reduced by Visage®. Eggers fails to describe any protrusion-recession tissue protecting energizable tip to reliably track without the formation of tunnels or remnant tunnel walls capable of creating uniform facial tissue planes upon which to uniformly transfer energy. Without uniform tissue planes to uniformly energize, there will cannot be uniformity of tissue contraction. Without facial uniformity there is only non-uniformity.

Eggers' U.S. Pat. Nos. 6,740,079 and 6,719,754 and 6,659,106 and 6,632,220 and 6,632,193 and 6,623,454 and 6,595,990 and 6,557,559 and 6,557,261 and 6,514,248 and 6,482,201 and 6,461,354 and 6,461,350 are virtually all bipolar in nature and require a fluid delivery element that may be located on the probes or part of a separate instrument. Alternatively, an electrically conducting gel or spray may be applied to the target tissue. All are incapable of yielding tunnel-wall-free, completely uniform facial planes upon which to energetically act thereupon. '559B1 does teach a single platypus-bill shaped, asymmetrically located, "atraumatic" shield which is totally incapable of yielding tunnel-wall-free, completely uniform facial planes upon which to energetically act since a single shield would create non-uniform tunnels and be deflected by them to a zone of least resistance. '354B1 requires that the bipolar electrodes be maintained "a distance of 0.02 to 2 mm from the target tissue during the ablation process . . . maintaining this space . . . translate or rotate the probe transversely relative to the tissue (brushing)". If coagulation or collagen shrinkage of a deeper region of tissue is necessary (sealing an imbedded blood vessel) . . . press the electrode terminal . . . Joulean heating." In itself, '354B1 would thus be impossible if not completely impractical device for use as an internal, minimally-invasive, complete facial tissue modification device because fulfilling such requirements of pressing blindly to seal unseen blood vessels up to 10 cm away from a limited incision port would impossible without an endoscope and thus take hours to complete surgery (less than opening up and closing an entire traditional face-lift). The handling of bleeding vessels, as per column 8 of '350B1, is surgically awkward without an endoscope and surgically impossible if performed blindly from limited incisions for the same reasoning as just mentioned for '354B1. '350B1 relies on the relative weakness of the electrical energy found in bipolar designs; circuitry detection and interruption with an alarm may fail to preserve nerves as opposed to applicant which relies on geometry to maintain precise location on motion and palpable feel to manipulate away from known nerve locations to avoid damage. Applicant and other facial surgeons disagree with Eggers statement in '261B2 that 150 degree Centigrade temperatures generated by probe's residual heat can seal vessels; those who disagree cite the example medium sized branches of the facial artery in the event of a bleed a hidden distance from minimally invasive incision sites. In all of Eggers, especially '193B1, FIG. 3, initial inspection of the two-dimensional figures may resemble those of applicant, however the protrusions are in a cylindrical base, conductive, non-insulated, not linearly arranged and do not have a lysing segment between them. '248B1 uses a laterally deployable and retractable antenna arising from the side of a pencil-shaped shroud-like probe to more precisely modify electrosurgical arcs for cutting of tissue. '248B1 differs from applicant by using a laterally based electrode and being unable to position said portion of the cutting instrument for uniform lysis of the delicate undersurface of the face. The lateral wire of '248B1 would be forced in a direction opposite the areas of greatest fibrous build-up adjacent non-uniformly lysed tunnels thus resulting in a non-uniform result. '079B1 is an electrosurgical generator capable of delivering uniform discharge arc at the tip and thus more precise cutting wave. '079B1 uses an active electrode with a dynamic active surface area of varying geometry however, applicant's geometry differs significantly in that '079B1 is incapable of yielding tunnel-wall free completely uniform facial planes which would adversely effect evenness in tissue plane energy absorption. Additionally, the monopolar cutting current of '079B1 is undesirable for collagen/fibrous tissue modification function of applicant's tissue-modifying-energy-window/zone and would largely damage the delicate underside of the facial dermis and dermal plexus since '079B1's stated and anticipated geometry lacks the protective insulated protrusions of applicant to safeguard such vital structures. Virtually all of Eggers teaches bipolar electrosurgery; as Eggers states, bipolar electrosurgery desirably create the following "plasma layer confines the molecular dissociation process to the surface layer to minimize damage and necrosis to the underlying tissues." To bring about significant uniform and safe modification of the overlying dermal and epidermal tissues without irregular defects such as necrosis is not possible without applicants geometry and adjacent energy function. Because of this lack of significant tightening efficacy without permanent epidermal changes or scarification, Visage® has seen only limited use in cosmetic surgery and salons; use at higher energy levels has caused undesirable surface skin scarring.

Goble, U.S. Pat. No. 6,210,405 teaches an electrosurgical rasping device that works similarly to Eggers. Goble teaches a "rasping" device that creates vapor bubbles requiring aspiration around the targeted tissue as opposed to applicant who teaches smooth forward instrument without rasping to wear down target surface. Goble teaches uses in orthopedic surgery and urological surgery requiring a saline like solution " . . . to fill and distend the cavity . . . " as opposed to Applicant and applicant's prior related art which does not. Goble teaches an instrument useful for "brushing . . . debulking . . . sculpturing and smoothing" as opposed to applicant who cuts and passes smoothly by the target tissue which is not to be removed but energetically altered and left in place to remodel. Gobel requires an ionic fluid pump and an aspirator and mentions the need for endoscopic assistance as opposed to applicant. Applicant teaches a feel-only, blindly operated device wherein pumps or aspirators are optional. Goble's teaches "rasping" as acting like a rasp to "wear down" as opposed to applicants prior use of the word "rasp" which just the feeling that the operating surgeon gets when the device passed successfully in the proper fibro-fatty facial tissue plane.

Thermage, Inc. of Hayward, Calif. recently introduced to the market its tissue contraction product of an externally applied electrosurgical template activated while touching the outer. Energy passes through the epidermis thus passing energy through the upper skin with the intention of electrically altering collagen to achieve remodeling; damage to the epidermis is reduced some by externally spraying a cryogen (cooling gas) of about −40° C. on the targeted zone's epidermis at the time of the electrical impulse. Unfortunately, the amount of tissue contraction Thermage, Inc. can prove in the medical literature borders upon statistical insignificance (to quote several prominent cosmetic surgeons) and is far less than 5%. Currently, great debate exists in the cosmetic dermatologic community as to whether a statistically significant improvement exists at all regarding Thermage's tissue contraction. U.S. Pat. No. 6,413,255B1 of Stern relates to Thermage's device and is an externally applied "tissue interface surface . . . and has a variable resistance portion." '255B1 teaches a linear array of externally applied bi-polar electrodes; an externally applied monopolar embodiment using return electrodes is also illustrated. Base claims in '255B1 regarding the electrosurgical delivery device indicate contact with the skin's external, outer surface. Knowlton U.S. Pat. Nos.: 6,470,216 and 6,461,378 and 6,453,202 and 6,438,424 and 6,430,446 and 6,425,912 and 6,405,090 and 6,387,380 and 6,381,498 and 6,381,497 and 6,337,855 and 6,377,854 and 6,350,276 and 6,311,090 and 6,241,753 and 5,948,011 and 5,919,219 and 5,871,524 and 5,755,753 are Thermage, Inc. licensed. Knowlton mentions in '498B1 "the methods of the present invention do not provide for total necrosis of cells. Instead, . . . a partial denaturization of the collagen permitting it to become tightened." Knowlton cites the failure of U.S. Pat. No. 5,143,063 to protect the melanocytes (pigment cells of the epidermis) as a need "for tissue tightening without damaging the melanocytes or other epithelial cells, or without surgical intervention." Knowlton's before-mentioned art is thus classified as non-invasive and therefore involving no incisions or intended openings even in the epidermis as a result of tissue damage. Applicant's art requires incisions as opposed to the before-mentioned art of Knowlton which is not mentioned to be inserted through the skin; Knowlton's devices are far to large to be adapted to any minimally invasive surgical sites. '854B1 Method for Controlled Contraction of Collagen in Fibrous Septae in Subcutaneous Fat is largely viewed in the medical community to be undesirable. Pulling on the septal strings cause in-pocketing of the surface skin. This because cellulite (an undesirable problem) is currently widely thought to be the result of contracted fibrous septae causing in-pocketings of the upper skin layers down toward the fatty layer. In '753B1 Knowlton desires to create no deeper than a second degree burn on the tissue surface to internally scar and thus create tissue contraction over areas such as a bony callus over periosteum and states, "This method is particularly useful in tissue sites that are devoid or deficient in collagen." In '753B1 Knowlton mentions that the device can be done transcutaneously, percutaneously or via endoscope, Knowlton also mentions reverse thermal gradients in that epidermal sparing results form heating below the surface. The principle of delivering electricity on a medical instrument under the skin is not novel, just the use of Knowlton's specific embodiment is. Similar percutaneous delivery of energy has however long been the practice of surgeons dating for electrosurgery at least from the mid 1980's and for laser surgery from the 1990's when Cook was directing lasers percutaneously to contract the underlying dermis of the neck. Much of the endoscopy art dating over one to two decades allows for percutaneous delivery electrosurgery and or laser. Most distinguishing is that '753B1 fails to provide a means to create a uniform planar tissue surface upon which to deliver electronic energy in a uniform fashion. Irregular target surfaces yield irregular electronic energy gradients. Applicant can provide a uniform band of freshly separated facial tissue to treat that is free of fibrous tunnel walls; thus, the overlying collagen can be uniformly treated by an underlying energy source and gradient without resultant striping or banding of the overlying skin including the epidermis. '753B1 provides no means nor an enablement to allow for a minimally invasive creation of a path in which to pass the '753B1 device freely without the formation of tunnels or breaking strong fibrous impediments. Knowlton in '276B1 displays a FIG. 2A showing an "introducer" that crudely in two dimensions resembles applicant; however, this is merely because the cylindrical 2A device with protruding attachment channels for cables, catheters, guide wires, pull wires, insulated wires, optical fibers, and viewing devices/scopes has been rendered only two-dimensionally whereas three-dimensional considerations reveal great dissimilarity. Knowlton's description in column 4 of '276B1 mentions the device coupling to a template to receive a body structure. '276B1 apparently mentions and designs for only external tissue (or other outer layer skin like mucosa) to be in contact with the template. The remainder of the group of patents are related to '090 and involve externally applied devices to the outer skin with ion permeable porous membranes using electrolytic solutions that at least partially conform over the external skin surface in a way similar to rubber ('202B1 teaches inflating a membrane for body conformation); monopolar and bipolar embodiments are presented. Such devices are intended to pass radiant energy (defined as any kind that can cause cell heating or physical destruction . . . including RF, microwave, ultrasound, etc.) through the epidermis in a uniform fashion and to minimize epidermal damage using cooling lumens and surface cooling fluids. Applicant and applicant's prior related art on the other hand teach an internal probe with a special tip that provides tunnel-free planar lysing precisely through human face while maintaining a tracking feeling. Nonetheless, following many published studies the energy applied through the simultaneously cooled epidermis of US '255B1 is insufficient provide a consensus on photographic wrinkle or tissue tightening improvement beyond mild. Conversely, Applicant and applicant's prior related art teaches energy levels that are much higher in fluence and bypass the ultrasensitive epidermis altogether. Applicant and applicant's prior related art does not necessarily require a cryogen spray to reduce epidermal heating so as to pass significantly greater levels of electrical energy into the targeted dermis.

Brucker, U.S. Pat. No. 5,500,0012 and other spot treatment combination energy devices using laser, fiberoptics, radiofrequency, ultrasonic or microwaves differ from Applicant and applicant's prior related art in their inherent shapes which are usually catheter like, bendable, circular in cross section. Flexible catheters cannot not penetrate the fibrous tissues of the face on their own. Such devices are usually meant to migrate between organs to perform a 'spot' treatment on one or more of them. It is to be noted in FIG. 4 of Brucker that electrodes 18 & 20 are detector electrodes meant to aid in the detection of electrical heart arrhythmias and that any similarity to the insulated protruding segments of Applicant and applicant's prior related art is clearly different when two dimensional drawings are considered in three dimensions just as was Eggers'. Brucker as a bendable catheter would not have the rigidity to course along the proper fibrous facial plane and would simply bore a hole or tunnel or be directed in a path of least resistance. The only similarity between Brucker and the instant application of Applicant and applicant's prior related art is that Brucker may carry fluids toxic to heart cells; however, applicant's use of prolotherapy with the device is to uniformly modify a uniformly created tissue plane. The arrays of electrodes in Brucker are detecting electrodes located around the tip of Brucker in which lies a single energized treatment electrode that only escapes or transiently protrudes from the catheter channel when there exists a need to kill heart cells that are improperly firing electrically; Brucker's protruding arrays are usually not deployed in motion and would likely interfere with motion by catching on tissues during motion, Brucker's protrusions therefore do not aid in device motion.

Single lumen, circular or non-planar cross sectional laser delivery devices such as Keller U.S. Pat. No. 5,445,634 & U.S. Pat. No. 5,370,642 usually require the use of an accessory endoscope. An endoscope is a cumbersome optical instrument that would usually requires two hands to use at the same time the surgeon is handling Keller's instrument to direct it to the target tissue which would be difficult indeed. Keller and similar devices differ by lacking applicant's planar tip configuration of protective relatively protruding non-conducting elements with energized relative recessions. Applicant's art can be manipulated blindly by the surgeon without the aid of an endoscope since the device provides instant continuous feedback via a simple palpable "feel" that the surgeon can easily learn and rely on for certainty that the device is migrating in the tissue properly. Devices such as Keller can only perform spot tunneling unless the surgeon is also using an endoscope that focuses some type of tissue dissociating energy along an entire tissue plane; unfortunately, to maintain a coordinated planar movement with Keller would be time-consuming and difficult. Keller discusses that results using '634 and '632 are limited to channels.

Loeb of U.S. Pat. No. 5,984,915 teaches passing only a single bare optical fiber through human facial subcutaneous skin tissue. Loeb however does not teach any housing or rigid or semi-rigid structure that would allow passage of a bare optical fiber through undissected tough and fibrous human fibro-fatty facial tissue. In line 55 column 6 Loeb states and alleges: "The optical fiber is a bare optical fiber . . . The tip pierces the skin and is advanced into the subcutaneous tissue while emitting laser energy . . . " Loeb further teaches in column 9 line 14: "The diameter of the tip of the optical fiber is in the range of about 25-100 microns (<0.1 millimeter) . . . Preferably about 50 microns . . . " Those skilled in the art readily know that it is impossible to advance such a thin fiber through relatively impenetrable human facial tissue to have any uniform clinical effect. Without uniformity on the face, one has deformity. In light of the human facial anatomy, where the dermis is composed of almost impenetrable collagen fibers close to the density of football leather and where the subcutaneous fatty layer contains collagenous fibrous septae that are relatively dense although not as dense as the fatty layer of abdomen, Loeb cannot deliver a uniform effect and is impractical as enable in '915. Applicant differs from Loeb because applicant provides for a relatively rigid structure housing energetic elements that can penetrate the extensive fibrous septal network of the facial subcutaneous layer and provide uniform tissue surfaces to enlarge thus altering the collagen of this layer of the face efficiently. Loeb teaches a pulsed energy level in Table 1 for "skin wrinkle removal", that even if the impossible task of passing a single hair thin optical fiber through the relatively dense facial fatty layer were possible then based upon Loeb's fiber diameter it would take many hours to days to efficiently irradiate or treat a whole face. It is noteworthy that under most facial wrinkles, collagenous accumulations are particularly dense further arguing against Loeb.

The term rhytisector is a compound word derived from (rhyti=wrinkle)+(sector=to cut or remove). The tool was usually inserted under the skin in a natural crease, fold or hairline a distance from the targeted wrinkle to be "removed". A rhytisector is a "Y" shaped device made of metal with the shaft/base of the Y usually being between 8 cm and 16 cm long and the arms of the V portion of the Y being about 3-4 mm and the base (acute angle) of the rhytisector is usually thin and cutting in nature. Rhytisectors discussed in the medical literature are completely flat when viewed horizontally from the side and not electrified energized in any way. Rhytisector use has decreased dramatically over the last decade. Unfortunately, the rhytisector tool developed a reputation for intense bleeding leading to bruising, hematomas (blood pools) and unwanted blood vessel laceration (breaking open). This was largely due to the sharp edges and no ability to coagulate. Applicant has searched catalogues from prior to 1999 of many major electrosurgical and plastic surgical/medical instrument manufacturers: Bernsco, Ellman, Colorado Biomedical, Conmed, Delasco, Snowden-Pencer, Tiemann, and Wells-Johnson and found no mention of any rhytisector that was electrifiable or substantially electrically resistive on the distal tips of the "Y". Even if a rhytisector was insulated similar to applicant the shape would be different since the rhytisector is a completely thin and equally flat instrument.

U.S. Pat. No. 5,776,092 by Farin describes a single tube device that can deliver laser, ultrasound or radio frequency devices to treat tissue. However, Farin's device is not intended for separating tissue planes and is susceptible to catching, tearing or puncturing the tissue when manipulated. The dissimilarities between Farin's device and those similar have been described in this application and those co-pending.

The dissimilarities of using ultrasonic liposuction cannulas for face-lifting or facial tightening from this patent application have been described in this application and those co-pending.

There exists a special subset of the general population that may benefit uniquely from the present invention. The facial skin and substructure of Caucasian men and women begins to droop and develop folds between the ages of 45 and 55. Patients of Asian, Hispanic and African origin will experience the same stage of this condition but at a bit later age. Currently long incisions of 10-20 cm are made around each of the two ears, for the purposes of hiding the scars; skin is cut out and discarded and the remaining skin stretched. Unfortunately, skin does not thicken in response to stretching and removal; it only thins. In the early 1990's, some plastic surgeons advocated "prophylactic" or "preemptive" face-lifting on women in their 40's purportedly to "stay ahead of nature." This philosophy of "prophylactic face-lifting" has now been largely discredited by the vast majority of reputable surgeons.

Given the disadvantages and deficiencies of current face-lifting and skin-tightening techniques, a need exists for a device that provides a fast and safe alternative. The present invention utilizes a unique energized lysing design adjacent to various similar and dissimilar forms of energy to induce tissue contraction. The present invention provides a process for human or animal tissue strengthening to achieve face-lifting, facial tightening, or non-facial tissue tightening. The device and methods can rapidly be used in hospitals as well as office-based surgery and minimizes pain and risk of injury.

SUMMARY OF THE INVENTION

It is an object of the present invention is to provide a method and a device that can be used by surgeons to provide quick and accurate face-lifting, tissue strengthening or tightening maneuvers is minimally invasive, rapidly performed with relatively speedy patient recovery while reducing pain and side effects.

It is another object of the invention to provide a surgical face-lifting device that easily maintains the proper dissection plane while uniformly lysing and offering the capability to deliver energy to uniform tissue planes to induce skin tissue tightening and strengthening.

Another object of the invention is to provide an undermining device that can position lysing surfaces at a proper level for controlled, safe and uniform fibro-fatty tissue separation during a face-lift that is tunnel-free and free of fibrous walls.

Tip shape and size definitions are as follows: bulbous—tip projection in the rough geometric or rounded shape of a bulb when viewed from the top or front when compared with a thinner adjacent lysing area; lysing segment—tip area that is thinned when compared with adjacent area in the shape of a bulb when viewed from the front; relative protrusion—tip projection in the rough geometric or rounded shape when viewed from at least one angle when compared with a thinner adjacent "lysing area" that would be relatively recessed; relative recession—areas of the tip that appear recessed as opposed to the relative projections when viewed from at least one angle.

The device is comprised of a hollow or solid shaft with a relatively planar tip that can be easily positioned and maintained between dissection planes in tissue and then manipulated to uniformly separate tissue planes and completely lyse fibrous tissue. It has been shown in a very limited fashion by Cook in the medical and others in the scientific literature that the effects of energy application to the collagenous (dermal, superficial platysma musculature and other) tissues of the face in the facelift plane can cause contraction and tightening. Accordingly, the invention also provides an energy source and delivering means, which delivers energy to the distal end of the shaft. Many forms of energy may be used to energize various portions of the device including multi-chromatic light, monochromatic light, laser light, radio frequency electrical energy, vibrational energy, ultrasonic energy, microwave energy, thermal energies both hot and cold, chemical energy or any combination thereof. Applicant can transmit significant energy to the subcutaneous tissue whereby the inflammation and mediators created cross the separated plane into the overlying dermis causing inflammation and contraction.

The preferred embodiment of the invention has a plurality of protruding members on the distal end of the shaft, referred to herein synonymously as tip, separated by at least one interstitial lysing segment, wherein the lysing segment is recessed relative to the protruding members. A planar, round or geometric shaft may terminate in some geometry of tip that is nonetheless substantially planar within a rectangle, somewhat curviform or geometric but somewhat off-plane. The tip shape when seen from above or below may vary and be rounded, squared, rectangular, serrated, scalloped, grooved, or geometric. Curved and lenticulate shapes may also be used. The tip shape when seen from the frontal view may vary and may include oval, rectangular, serrated, scalloped, grooved, or geometric. Although one favored embodiment provides a shaft that has a cross-sectional shape that is flat or planar, acceptable alternative versions of the shaft may be oval, circular, trapezoidal or geometric on cross-section. Although an embodiment provides a tip having a shape with alternating protrusions and recessions, acceptable alternative versions of the tip shape may be semicircular, lenticulate or geometric.

For mid and lower face-lifting/tightening the surgeon makes three or more relatively small incisions only in the skin in front of the ears and under the chin. Forward and lifting force are then applied to the shaft of the device by the surgeon's hand to uniformly separate and maintain tissue planes while the shape of the device excludes critical structures (nerves, vessels) thus avoiding entanglement or trauma or indiscriminate cutting of these important structures. The same protrusions (in the most-preferred embodiment) that exclude critical structures by virtue of their relationship to the cutting recessed segments also serve to position the depth of the present invention with respect to the lower dermis. The spacing of the relative protrusions (bulbs) and relative recessions (lysing segments) maintains the tracking of the instrument. The beneficial feeling of "tracking" is instantly palpable by the surgeon on device motion and requires no monitor to know how the device is moving. Both the number and spacing of protrusions in one embodiment will aid in reducing wobble or lateral (horizontal) slippage during forward thrusting of the shaft. Vertical slippage is prohibited as well in one embodiment; the width of the protrusions/bulbs maintains the correct distance between the lysing/recessed segments and a portion of the delicate underside of the superficial skin or dermis containing the vital blood supply from the dermal plexus of vessels. Very beneficially, the tip of the device and the action of the device can be felt/appreciated without direct visualization (endoscope). The surgeon can palpably feel whether the device is tracking in the proper location; the feel of the device as it moves with palpable and easily grade-able resistance through the facial tissues can immediately tell the user the location and the amount of undermining that has occurred at that location. Uniquely, this device creates uniform tissue planes which can be uniformly energized. No fibrous walled tunnels or non-uniform irregular fibrous ridges are left following passage that would fall prey to irregular energy gradients.

Embodiments using a Protrusions/Recession version, a Laser-Energized version, a Monochromatic/Polychromatic Light version, a Thermal version, a Low-Mid Frequency "Regular" Ultrasound-Energized version, a High-Frequency Ultrasonic-Energized version, a Reciprocating Energy version, and Electrosurgical/Radiofrequency-Energized version, a Thermal/Heating-Iron-Energized version, and a Microwave-Energized version have been described in this application, those co-pending and issued.

Prolotherapy (nontraditional) may be used in conjunction with the instant surgical device. The use of the instant surgical device provides a unique for prolotherapy to affect precisely separated facial tissue planes. The use of prolotherapy (traditional or nontraditional) has not, to our knowledge, ever been described in conjunction with an internal approach to skin rejuvenation. If one considers prolotherapy to be the injection to irritating compounds into the body to stimulate a vigorous collagenous response then the above conclusion is true. It may be argued that external approaches to stimulating fibroblast/collagen reformation of the surface skin such as deep chemical peeling (with chloroacetic acids or phenol), however their effects cannot reach the deepest aspects of the skin without gross and permanent deformity of the surface skin: the delicate epidermis.

The following is a brief background on the uncommon topic of prolotherapy taken from the available medical literature. Prolotherapy is also known as nonsurgical ligament reconstruction, sclerotherapy, sclerosant therapy and regenerative injection therapy. In the 1950s, Dr. George Hackett, a general surgeon, theorized that chronic musculoskeletal pain often resulted from lax ligaments and tendons (Hackett G S. Ligament and Tendon Relaxation—Treatment by Prolotherapy. $3^{rd}$ ed. Springfield, Ill.: Charles C. Thomas Publishers; 1958:1-151). Hackett injected glucose solutions into tissues to induce a fibroblastic response resulting in scar tissue formation and ligament and tendon strengthening. Hackett termed this treatment prolotherapy, derived from the Latin word meaning to proliferate. Since its original description, prolotherapy has been used for treatment of a variety of musculoskeletal conditions, including osteoarthritis, back pain, neck pain, fibromyalgia, and whiplash headache among others. A variety of sclerosing or proliferative solutions have been used in prolotherapy injections including hypertonic glucose (D-glucose), sodium morrhuate, and phenol. Injections are ideally placed near the affected tendon or ligament-to-bone junction with avoidance of direct ligament injection as this has the potential to cause ligament destruction and rupture. The most common adverse effect is pain at the injection site (Kim S R, Stitik T P et al. Critical review of prolotherapy for osteoarthritis, low back pain, and other musculoskeletal conditions: A psychiatric perspective. *Am J Phys Med Rehabil* 2004;83:379-389). Case reports and case series have reported improvement in patients with chronic headache and neck pain treated with prolotherapy but have lacked adequate control groups for comparison (Abraham I. Prolotherapy for chronic headache. *Headache* 1997;37:256). Randomized and quasi-randomized controlled trials have examined the efficacy of prolotherapy in the treatment of chronic back pain, in many cases in patients in which standard therapies have failed (Kim S R, Stitik T P et al. Critical review of prolotherapy for osteoarthritis, low back pain, and other musculoskeletal conditions: A psychiatric perspective. *Am J Phys Med Rehabil* 2004;83:379-389. Yelland M, Glasziou P et al. Prolotherapy injections, saline injections, and exercised for chronic low-back pain: a randomized trial. *Spine* 2003;29:9-16. Yelland M, Mar C et al. Prolotherapy injections for chronic low-back pain. *Cochrane Database Syst Rev* 2004;2:CD004059). Although studies have shown some benefit of prolotherapy for back pain, data cannot be pooled for meta-analysis due to clinical heterogeneity among studies; study results are confounded by a lack of adequate controls and the presence of co-interventions (Kim S R, Stitik T P et al. Critical review of prolotherapy for osteoarthritis, low back pain, and other musculoskeletal conditions: A psychiatric perspective. *Am J Phys Med Rehabil* 2004;83:379-389. Yelland M, Mar C et al. Prolotherapy injections for chronic low-back pain. *Cochrane Database Syst Rev* 2004;2:CD004059). Prolotherapy has shown some promise in the management of osteoarthritis of the thumb and fingers with 10% dextrose injections, although study sizes have been small (Reeves K D, Hassanein K: Randomized, prospective, placebo-controlled double-blind study of destrose prolotherapy for osteoarthritic thumb and finger (DIP, PIP, and trapeziometacarpal) joints: Evidence of clinical efficacy. *J Altern Complement Med* 2000;6:311-20).

A commonly used list of prolotherapy sclerosing or proliferative solutions includes glucose, sodium morrhuate, and phenol. The effects of such chemicals on human tissue may be thought of as controllable trauma to induce a fibroblast/collagen response. However, it stands to reason that other solutions that are relatively nontoxic to animal tissue in lower concentrations but caustic, irritating or toxic in some dose-dependent or higher concentrations can also serve well in prolotherapy and may include, but should not be limited to, other sugar solutions, polidocanol, salts (ie, NaCl), sodium docecyl sulfate. Such solutions can be injected into the pockets lying between the surgical planes created by the minimally invasive surgical device. Chemically induced tissue irritation or trauma will develop in the areas thus initiating a local fibroblastic response with collagen and tissue ground substance production, fibroblast proliferation and resultant tissue tightening and rejuvenation. The aforementioned agents are solutions, however the use of non-solutions including micelles, foams and suspensions or even mixtures of insoluble materials could bring about similar fibroblast/collagen tissue responses. Non-solutions that can irritate or controllably traumatize human tissues into a fibroblast/collagen response could include, but should not be limited to, silicone/ saline suspensions, collagen suspensions, fat globule/oil water suspension, sand, glass, plastic granules, other insoluble granules, soaps, ground microbiological, plant or animal matter. These type of materials would cause a microgranulomatous response with collagen/fibroblast proliferation. Of course all of the above materials would be injected sterile into the pocket and any excesses evacuated or drained at the appropriate treatment time period.

For decades plastic surgeons have inserted biological and non-biological, organic and inorganic meshes into the face to remedy defects and lend support, and other areas such as the abdomen and groin to lend support and to hold back herniated tissues. However, placement of the meshes necessitated much larger surgical openings than would be necessary with applicant and co-pending which are uniquely able to allow large potential free surface areas for mesh to be implanted upon while fitting such large meshes through only minimally invasive incisions.

The present invention can be used to improve the efficacy and safety of face-lifting and face-tightening and is thus useful in a variety of cosmetic procedures. The forgoing and other objects, features, and advantages of the present invention will become apparent from the following description and accompanying drawings.

BRIEF DESCRIPTION OF THE DRAWINGS

FIG. 5E is a top view of the tip area of the apparatus with a focus on the relative recession. Also shown are various possible locations with respect to it for the electrosurgical lysing element (left to right): recessed inside the relative recession or flush with the relative recession or protruding out from the relative recession.

DETAILED DESCRIPTION OF THE INVENTION

The present invention is a device that can be used by surgeons to provide quick and accurate face-lifting maneuvers minimizing the tissue trauma and removal. The device is comprised of an undermining shaft that can be easily positioned between dissection planes in tissue and moved forward to separate tissue planes by lysing all the connecting fibrous tissue without the formation of tunnels or fibrous walls. Embodiments of the invention provide for a substantially planar application of tissue-altering energy and/or chemicals to the newly created tissue surfaces. Sensors monitor tissue values such as temperature, inductance with feedback and control electronics control tissue altering energy or flow for optimal tissue contraction.

Figure 1A:
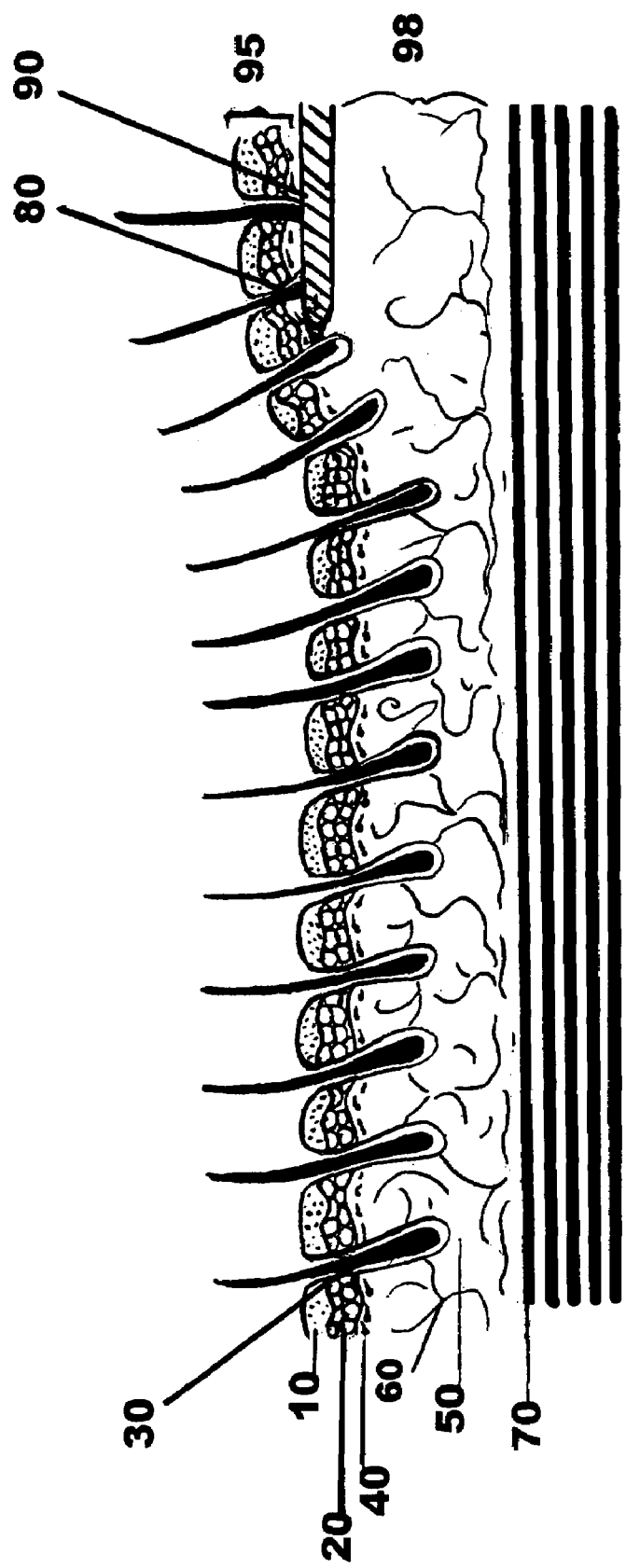
FIG. 1A shows pertinent layers and critical structures of the skin including the epidermis, dermis, hair follicles, subdermal plexus of blood vessels, subcutaneous (fatty layer) and the fibrous attachments. Also shown is location of invention's action in relation to these layers.

FIG. 1A shows a side view of various layers of the skin including the epidermis 10, dermis 20, hair follicles 30, subdermal plexus of blood vessels 40, subcutaneous (fatty layer) 50 and the fibrous attachments 60 extending from the dermis through the subcutaneous to the deeper facial structures 70. The subcutaneous layer of the face may best be thought of as the fibro-fatty layer indicating its tough fibrous nature. Preservation of the subdermal plexus of vessels has allowed surgeons to lift faces for most of the last century by hiding face-lift incisions around the ear even while cutting the blood supply of the surface skin all the way back to the lips, nose and neck. This is possible because, unlike most areas of the body (where the blood vessels supply the surface skin from directions perpendicular to the surface), the majority of the blood supply to the face upper neck is tangentially carried by the blood vessels of the subdermal plexus. By uniformly sparing the subdermal plexus blood from the lips, nose and neck surgeons can maintain the blood supply for complete tissue life in the upper facial flap even following the irregular trauma of the traditional extensive procedure. Collagen plays a critical role in the structure and support of the entire body especially the face; this basic structural protein is present in up to 5% of the epidermis, 50% of the dermis and about 20% of the subcutaneous layer depending upon the race, location, age and previous history of trauma in the patient. In the face, the subcutaneous collagen percentage can be significantly higher if the fatty content decreases due to many factors. Much of the subcutaneous collagen is present in the dense fibrous-septae of the fat. Also shown progressing from the right toward the left are the relative protrusions 80 of the special tip 90. Hidden from view are the relative recessions containing the tissue the lysing segments (unseen in this view) as they track to create a superior, mostly dermal, uniform tissue plane 95 separated from the mostly fibro-fatty inferior tissue plane 98. Note Applicant's device geometry spares the delicate subdermal plexus by positioning lysing segments during passage. The unique geometry of the tip upon the proper motion of the device through human or animal flesh gives the surgeon straight tracking feeling with a characteristic rasping sound and sensation which facilitates easy learning and beneficially allows virtual blind operation of the device using solely feeling. The lysing tip 80 passes through the level of the lower portions of the hair bulbs 30 thus destroying the hair bulb and causing a high percentage of hair removal. Hair removal or reduction is a potential benefit in the beard region of men especially those suffering from folliculitis of the beard region.

Figure 1B:
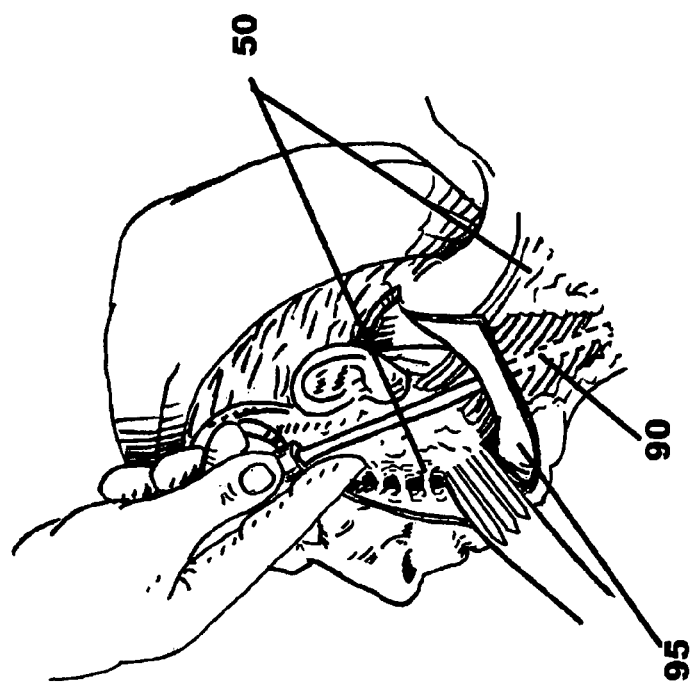
FIG. 1B is adapted from the classic textbook of plastic surgeons Baker and Gordon, *Surgical Rejuvenation Of The Face* showing the pattern of passage of a cylindrical object (differing from applicant) in the subdermal fibrofatty layer of the face that will result in the irregular, ridge-like, tunnels and walls.

FIG. 1B is adapted from the classic textbook of plastic surgeons Baker and Gordon, *Surgical Rejuvenation Of The Face* (Baker, Thomas and Gordon, Howard; C.V. Mosby Co., St. Louis, Miss., 1986) showing the pattern of passage of a cylindrical object 90 (differing from applicant) in the subdermal fibrofatty layer 50 of the face. Note the open flap 95 pulled by a surgical rake consisting mostly of dermis with some dermal plexus attached. This same pattern of passage of the cylindrical object will generate the irregular, ridge-like, fibrous tunnels and walls seen in FIG. 1C.

Figure 1C:
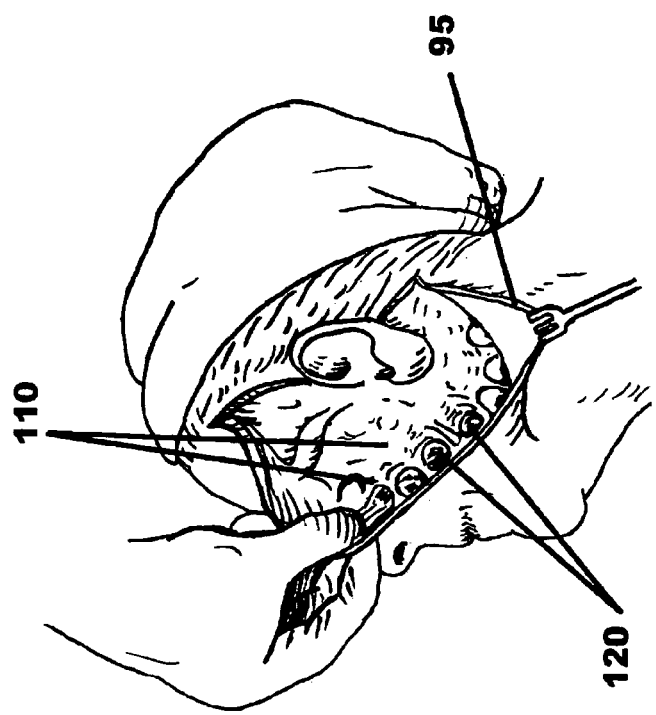
FIG. 1C is adapted from the classic textbook of plastic surgeons Baker and Gordon, *Surgical Rejuvenation Of The Face* showing the irregular, ridge-like, dense fibrous attachments associated with tunnels and walls that result from passage of a cylindrical object (differing from applicant) in the subdermal fibrofatty layer of the face.

FIG. 1C is adapted from the classic textbook of plastic surgeons Baker and Gordon, *Surgical Rejuvenation Of The Face* showing the irregular, ridge-like, dense fibrous attachments associated with tunnels 120 and walls 110 that result from passage of a cylindrical object (differing from applicant) in the subdermal fibrofatty layer of the face. Note that the undersurface of the dermal, or top leather layer of the skin flap 95, now held by a forceps, will have the irregularly thickened ridge like pattern attached to its undersurface. The irregular ridges on both sides of the lysed plane in three-dimensions look similar to the stalactites and stalagmites of a cave. The irregular ridge like pattern on the underside of the dermis would irregularly absorb energy applied to the undersurface. Non-uniform energy absorption yields non-uniform results; non-uniform results in the face are deformity. Also shown is the extent of the incision length used in the most common method for a traditional face lift, being over 30 cm in length, to expose a good view of the fibrous tunnels and walls. The surgeon can then scissor or scalpel cut the walls and connect the tunnels using the naked eye, however, scissors and scalpel cannot fit nor be safely done through the minimally invasive incision sites that applicant uses. Again, only applicant geometry can fit through the minimal 1 cm incision without expanding the incisions and do the separation in under 20 minutes that currently experienced plastic surgeons need the large exposed flap to allow proper visualization and larger instrument cutting.

Figure 1D:
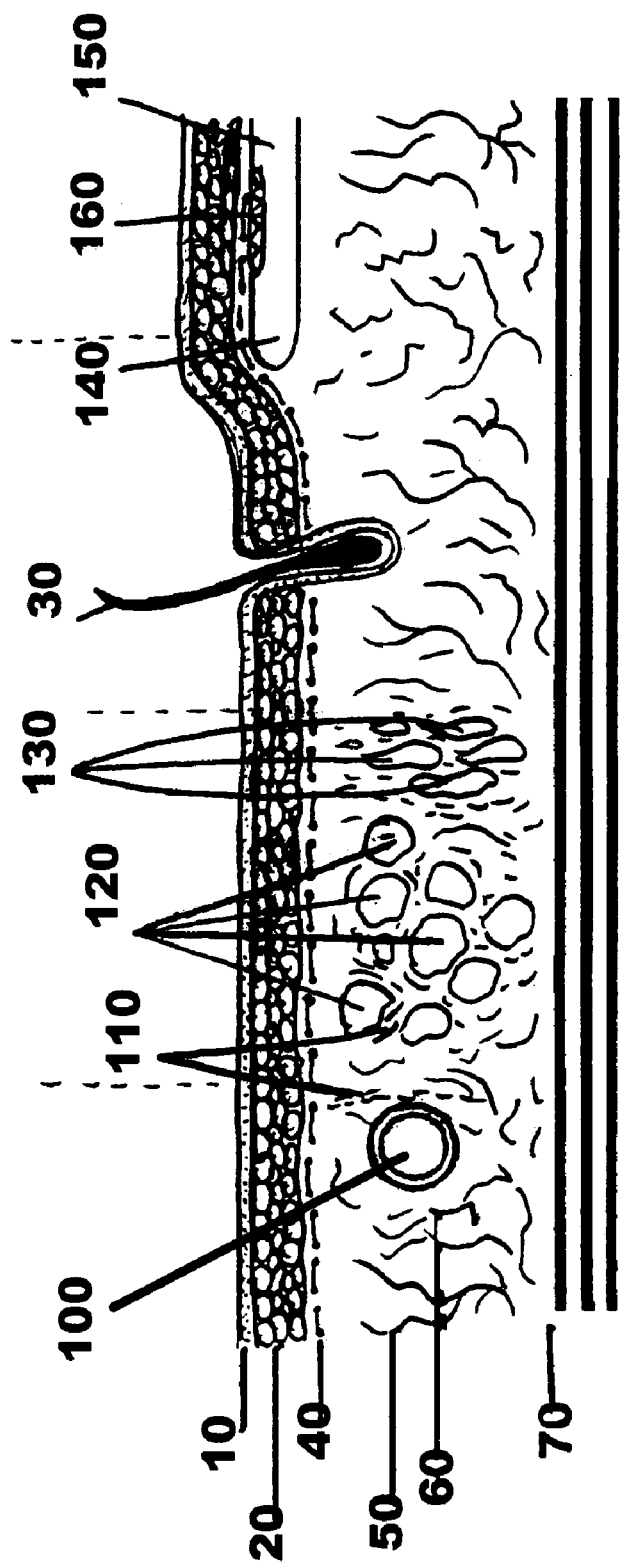
FIG. 1D shows a side view divided into quarters of same layers of the skin. Each quarter shows a view of the location and result of passage of differing classifications of energized probes and tip configurations. Applicant is displayed on opposite quarters for contrast.

FIG. 1D shows a side view of same layers of the skin including the epidermis 10, dermis 20, hair follicles 30, subdermal plexus of blood vessels 40, subcutaneous (fat) 50, and the fibrous attachments 60 extending from the dermis through the subcutaneous to the deeper facial structures. The far left half quarter of this figure displays a typical cylindrical tip 100, as viewed from the front, representing tip geometries other than the Applicant. However, virtually all other tip shapes including spatula, single protrusion, recessions from a single or non-uniform tip, beveled, semicircular, spoon-like, chisel, flat suffer from problems similar to cylindrical tips: unwanted tunnel formation with irregular, thick, remnant denser fibrous walls. The mid left quarter of this figure shows the instantaneous results of passage of a representative cylindrical tip (non-Applicant geometry), as viewed from the front. Note the "Swiss cheese" like hole-effect 120 with denser fibrous-septal-walls 110 & 130 separating the holes as a result of the passage. Unlike a mountain road tunnel forming device that slowly drills, grinds, removes and spits back all the hard rock before moving forward, none of the art to date is powerful enough, even the liposuction versions (after numerous passages) to completely remove all the soft fat in its path, let alone remove fibrous-septal-walls. Even if such devices were this aggressive, excessive removal of facial fat leaves patients with what surgeons desperately try to avoid and seek to correct: a skeletonized hollow look. It is the plump wrinkle-filling fat in the face that greatly contributes to a youthful appearance. The loss or descending of facial fat from normal positions contributes an aging look to the face. Disadvantageously, very little of the fibrous tissue in the path of the current art can be completely removed or vaporized, especially the dense collagenous fibrous septal walls which are known to make up a good portion of the human facial fatty underlayer. The already dense septal collagen is thus compacted into even more dense, potentially energy absorbing, collagenous fibrous-septal-walls -110- following non-applicant-tip-geometry instrument passage. The compaction and displacement of the collagenous septae following axial passage through minimal incision sites using non-applicant-tip-geometry results in highly irregular denser fibrofatty walls especially forming ridges 120 attached to the dermal underside. Furthermore, immediately following passage of non-Applicant-tip-geometry, the tunnels collapse into tissue slots 130 that may be oriented in many irregular directions as shown in the left half of the figure. In the middle right part of FIG. 1b, progressing from the right toward the left, is the relative position of the of applicant's dermal plexus protecting lysing tip 140 and attached shaft 150 having come from the far right after uniformly separating the tissue planes without leaving irregular fibrous walls or ridges. On the distal superior end of the shaft is the planar-tissue-altering-window/zone 160 which may accommodate various forms of energetic devises or tissue-altering chemical dispersing ports as described in applicant's and co-pending art. Note the uniformity of the tissue planes that are formed on the right side of the diagram and the absence of irregular dense fibrous septal compactions. Irregular dense fibrous septal compactions would irregularly absorb applied tissue-modifying energy and irregularly expose the target tissue to chemical gradients.

Figure 2:
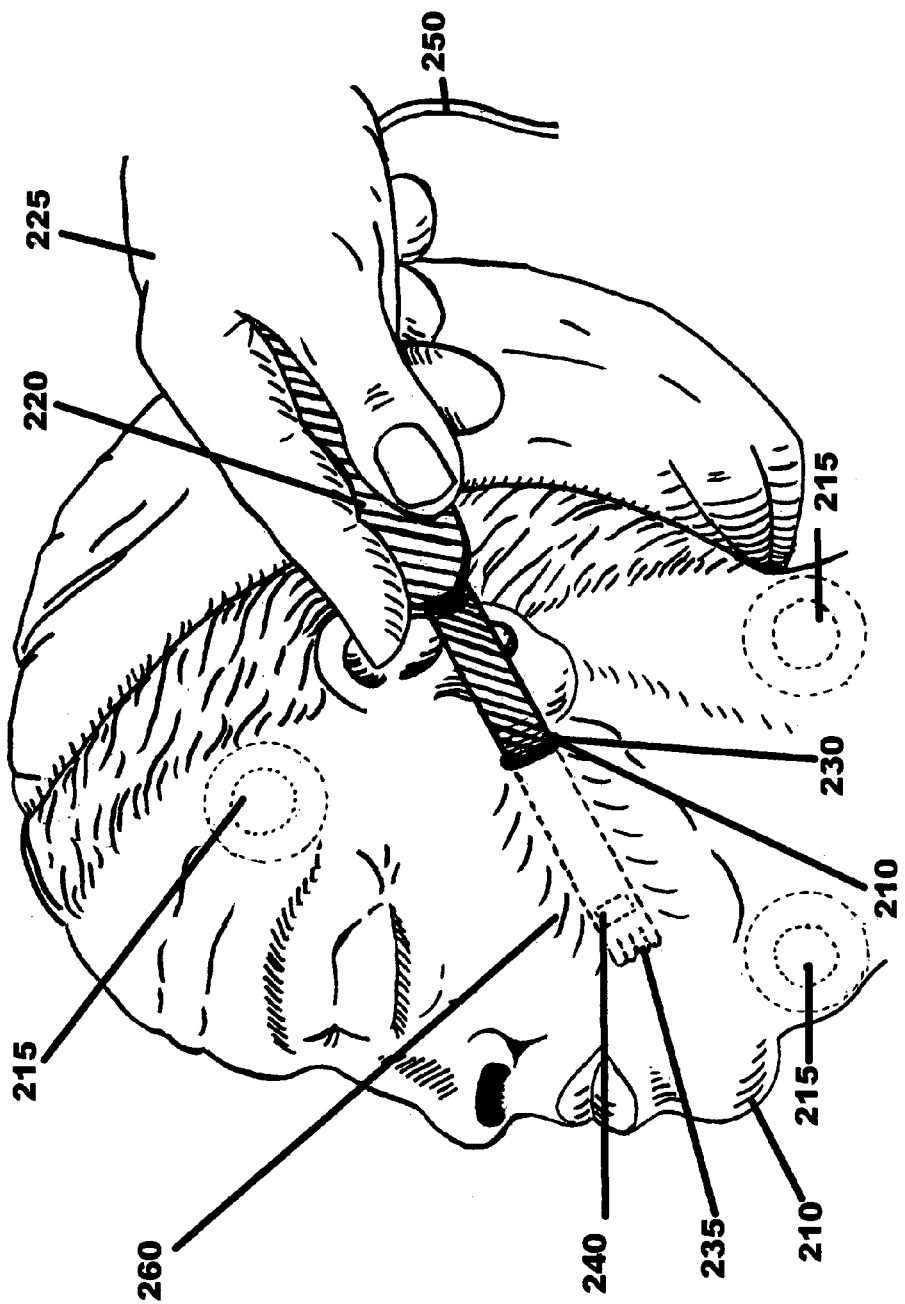
FIG. 2 shows a lateral or side view of typical incisions and points of insertion for 20 the facial tightening and strengthening device, manipulation of the device, and superficial nerve path locations.

FIG. 2 shows location and orientation of minimally invasive facial incisions which are the points of instrument insertion 210 through the epidermis and dermis for the facial tightening and strengthening device. Also shown are double dashed circles 215 around superficial nerve paths which all present day plastic surgeons currently avoid during face-lifting and which are also recommended not to be undermined with any energized device including applicant's. Even the use of smooth nonenergized liposuction cannulas in these zones has been well reported in the medical literature to cause temporary or permanent damage to the delicate motor nerves of these areas resulting in palsy. The partial top view of the face-lift apparatus of the present invention shows how the handle 220 of the apparatus is be gripped in the hand 225 of the user of the device. The shaft 230 with the special lysing tip 235 of the face-lift apparatus is inserted through standard openings in the skin 210 or at other suitable locations on the face of a patient. Single dashed lines indicate the portion of the device hidden from view under the skin. Curved stretch lines 260 indicate the upward force applied on the device and shaft 230 slightly tenting the overlying skin of the face. The apparatus is firmly pushed forwardly while being lifted forcefully by the operator to perform its function and maintain the plane of undermining. On the distal superior end of the shaft is the planar-tissue-altering-window/zone 240 (dashed and hidden from clear view in this representation) from which various forms of energy and tissue-altering-chemicals are allowed egress. Tissue altering energy and or chemicals traverse a portion of the length of the apparatus to planar-tissue-altering-window/zone via energy delivery and matter delivery means contained in conduit 350 and external line. An accessory conduit may travel along the underside of the device opposite the tenting skin side to maintain a streamlined shape if greater space is necessary than available in the shaft. The handle may contain an optional ultrasonic transducer piezoelectric and thus may impart ultrasonic energy to the shaft and tip facilitating passage of the instrument through fibro-fatty tissue.

Figure 3:
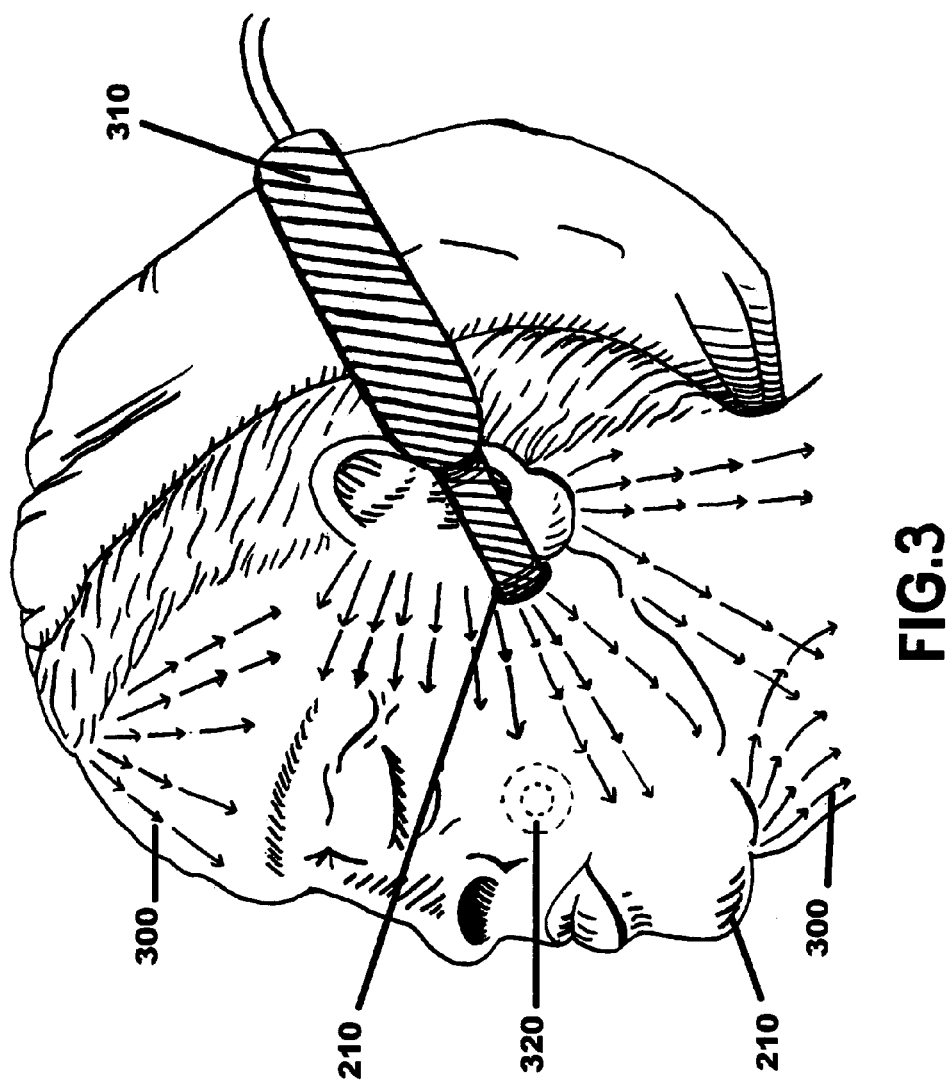
FIG. 3 shows a side view of points of insertion and vectors of tissue passage.

FIG. 3 shows a side view of location and orientation of minimally invasive facial incisions 210 as well as arrows showing the vectors 300 of planar passage for the facial tightening and strengthening device 310. Contraction along the direction of the vectored lines is beneficial since these are the customary tension lines that plastic surgeons stitch in parallel to re-create youth during a traditional face-lift. By meticulously using scissors and scalpel, plastic surgeons strive to avoid injuring the subdermal plexus blood supply during tissue plane separation so as to allow blood from the lips, nose and neck to flow through to the tissues supplied by remaining plexus vessels of the of the traditional face-lift flap. Since Applicant's device is meant to pass from only several incision sites, as opposed to cutting around the entire ear and temple, an even greater blood supply is available from the subdermal plexus to nourish the healing skin following applicant's method. Reductions in energy delivery are at greater distances (areas 320 demarcated by double dashed lines) of facial plane lysis from the remaining available blood supply attachment. These reductions minimize distant plexus and surrounding tissue trauma and therefore lessen the healing tissue nourishment burden.

Figure 4:
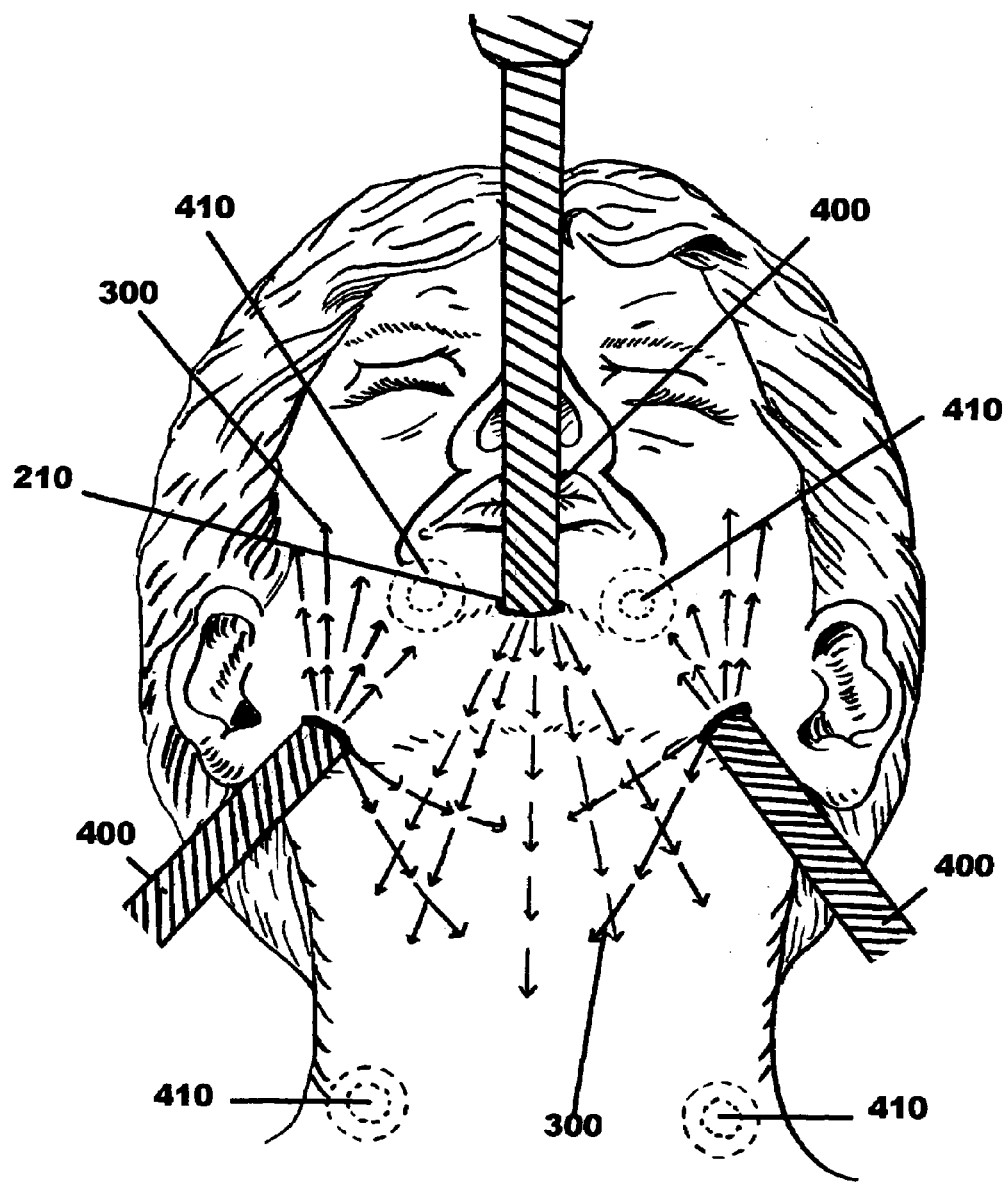
FIG. 4 shows a frontal view looking upward of typical incisions and points of insertion for the facial tightening and strengthening device, and superficial nerve path locations.

FIG. 4 shows a frontal view looking upward at typical incisions and points of insertion 210 as well as arrows showing the vectors 300 of planar passage for the facial tightening and strengthening device 400. Note again, the same double dashed circles 410 around the same superficial nerve paths to be avoided as seen from this view.

Figure 5A:
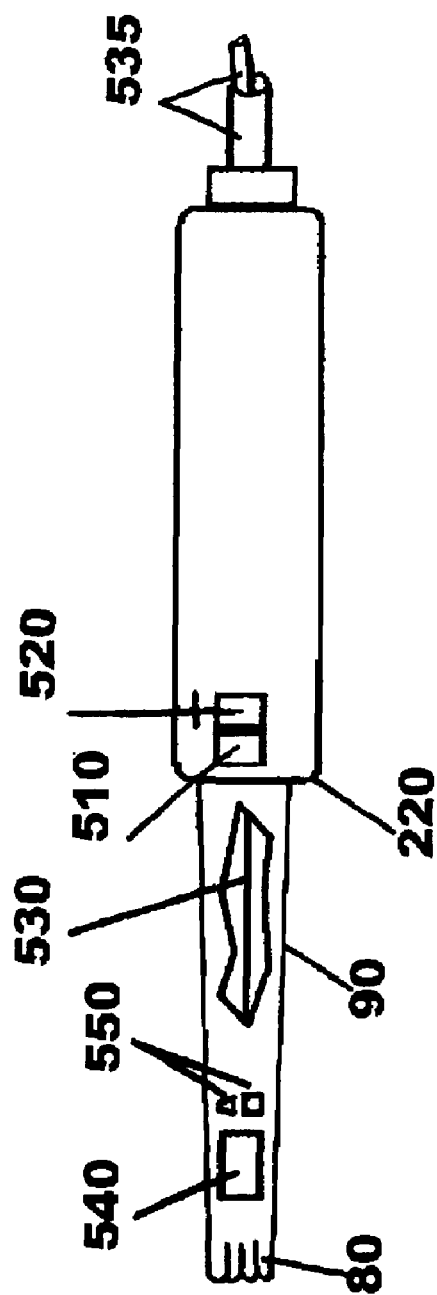
FIG. 5A is a top view of the apparatus with a focus on the distal shaft and tip region.

FIG. 5A is a top view of the face-lift apparatus. The tip 80 may be slightly larger than the shaft 90. Handle 220, coagulation and cut finger control buttons 510 leads to tip and 520 lead to tissue-altering-window/zone. However, the tip is preferably 1 cm in width and 1-2 mm in thickness for standard facial work and may be somewhat larger or smaller than the shaft. Sizes one-fifth to five times these dimensions may also have a need and find a use. For specialized work such as the eyelids, a proportionately smaller device, shaft and tip may be used of 2-4 mm in width. The tip can be a separate piece that is secured to shaft by a variety of methods such as a snap mechanism, mating grooves, plastic sonic welding, etc. Alternatively in this model, tip can be integral or a continuation of shaft made of similar metal or materials. The tip may also be constructed of materials that are both electrically non-conductive and of low thermal conductivity; such materials might be porcelain, ceramics, glass-ceramics, plastics, varieties of Teflon®, carbon, graphite, and graphite-fiberglass composites. Additionally, the tip may be constructed of a support matrix of suitable insulating material (e.g., ceramic or glass material such as alumina, zirconia: Kyocera Industrial Ceramics Corporation, Elkgrove, Ill.). Sealing material for a ceramic embodiment should have a compatible thermal expansion coefficient and a melting point differing from that of platinum or titanium and alumina or zirconia, typically being a glass or ceramic. A favored ceramic for tip construction is Forsterite of 2.9 g/cm3 density, flexural strength of 1500/kg/sqcm, temperature expansion coefficient (83+/−5) 10E-7, composition: $Al_2O_3$ 0.8%, $SiO_2$ 41.7%, MgO 51.5%, BaO 6%. Another favored ceramic for tip construction is BK 94-1 (Russian Index), flexural strength of 3200/kg/sqcm, composition: $Al_2O_3$ 94.4%, $SiO_2$ 2.8%, $MnO_2$ 2.3%, $Cr_2O_3$ 0.5%. An external power control bundle -535- connects to electrically conductive element or wiring -530- brings RF electrosurgical energy from an electrosurgical generator down the shaft to electrically conductive lysing elements mounted in the recessions. The tip may alternatively be made partially or completely of concentrically laminated or annealed-in wafer layers of materials that may include plastics, silicon, glass, glass/ceramics or ceramics. Alternatively, the tip may also be constructed of insulation covered metals or electroconductive materials. The shaft is usually flat, rectangular or geometric in cross-section or can be a somewhat flattened. Smoothing of the edges of the shaft reduces friction on the skin surrounding the entrance wound since it is the apex of repetitive spokewheel passages. The shaft may be made of metal or plastic or other material with a completely occupied or hollow interior that can contain insulated wires, electrical conductors, fluid/gas pumping or suctioning conduits, fiber-optics, or insulation. Shaft plastics, such as Teflon® may act as insulation about wire or electrically conductive elements. Shafts of any metal or alloy must contain sufficient insulating materials within to prevent unwanted discharge or conduction between internal elements and the shaft or tip. The shaft may alternatively be made partially or completely of concentrically laminated or annealed-in wafer layers of materials that may include plastics, silicon, glass, glass/ceramics, ceramics carbon, graphite, graphite-fiberglass composites. Depending upon the embodiment, an optional electrically conductive element internal to shaft conducts electrical impulses or RF signals from an external power/control unit (such as a Valleylab electrosurgical generator, Valleylab, a division United States Surgical of Norwalk, Conn., a further division of Tyco Healthcare) to the planar-tissue-altering-window/zone 540. Note that the planar-tissue-altering-window/zone is meant only to be relatively planar and may even take on a shape that represents a portion of the shape of a shaft, therefore somewhat arced or stairstep or other geometric modifications of the window/zone are possible. The conduit also contains the necessary electrical control wires necessary for device operation. Hidden from this direct view in this diagram, and located at the most proximal portion of the groove of a relative recession is electrically conductive tissue lysing element, powered by electrosurgical generator, which effects lysing of tissue planes on forward motion of the device and is located at the terminus of conductive element. Optional locations for multiple impedance sensors or multiple thermal sensors 550 which are used to monitor the local post passage electrical impedance and thermal condition exist near the distal tip of the shaft. Temperature and impedance values may be tracked on a display screen or directly linked to a microprocessor capable of signaling control electronics to alter the energy delivered to the tip when preset values are approached or exceeded. Typical instrumentation paths are widely known such as thermal sensing thermistors feed to analog amplifiers which in turn feed analog digital converters leading to a microprocessor. Internal or external ultrasound measurements may also provide information which may be incorporated into a feedback circuit. An optional mid and low frequency ultrasound transducer can also be activated to transmit energy to the tip and provide additional heating and improve lysing. A flashing visible light source, for example an LED can be mounted on the tip to show through the upper skin flap to identify the location of the device.

Figure 5B:
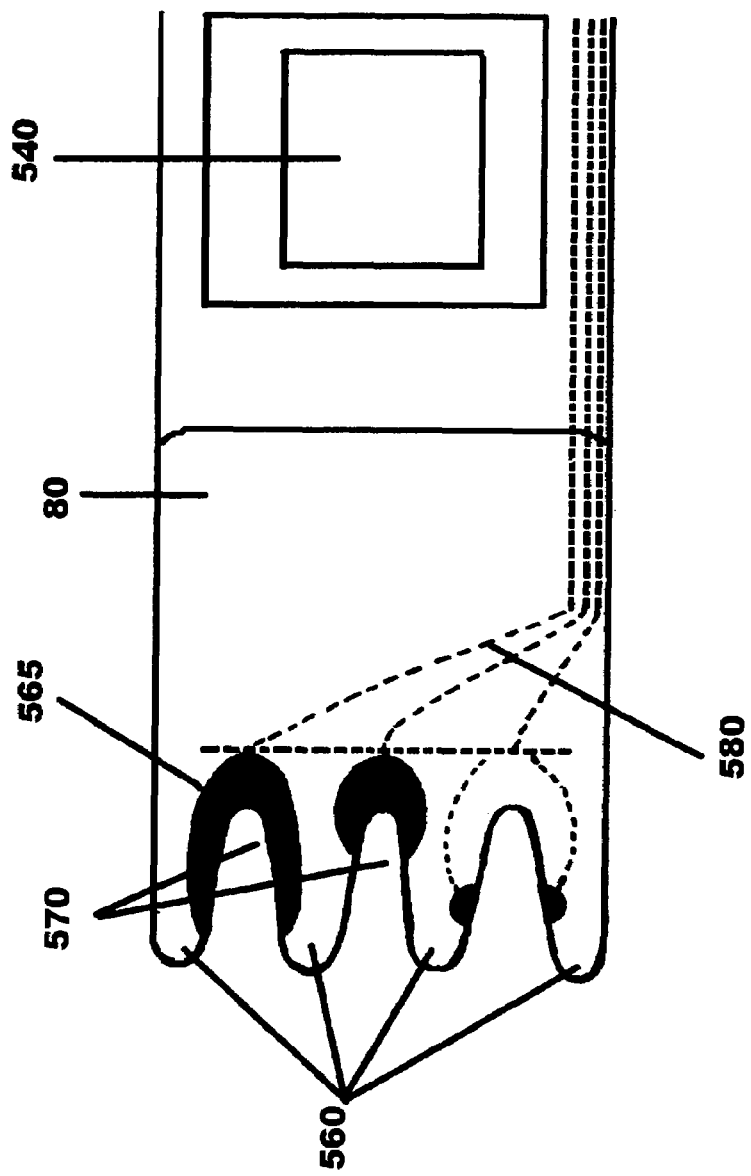
FIG. 5B is a top view of the tip area of the apparatus with a focus on the areas of relative protrusion and relative recession.

FIG. 5B is a top view of the tip area of the face-lift apparatus. The tip 80 is made of materials that are both electrically non-conductive and of low thermal conductivity such as porcelain, epoxies, ceramics, glass-ceramics, plastics, or varieties of Teflon®. Alternatively, the tip may be made from metals or electroconductive materials that are completely or partially insulated. Note the relative protrusions 560 and relative recessions 570 visible from this viewing angle. For the purposes of this and related applications we shall define or qualify a device as having protrusions and recessions at the tip if, when viewed three-dimensionally from at least one angle, then at least two relative protrusions and at least one relative recession can be seen. In order to protect the subdermal plexus of blood vessels, the protrusions are usually nonconductive electrically and minimally conductive thermally. Various materials may insert into, pass along, associate with, project from, or further recess into the concavity of the relative recessions; these materials are usually electrically conductive which we will name electrically conductive lysing elements. The tip shown in this embodiment, has four relative protrusions and three relative recessions. Electrically conductive lysing elements 565 are seated into the relative recessions. This particular embodiment in FIG. 5B provides for a monopolar tip conductive element. Note the relatively oval-protrusions are shaped similarly to a commercial jetliner nose cone in order to reduce drag and lower resistance to facilitate tissue passage. However, the tip protrusion shapes may take on a wide variety of geometric shapes including but not limited to stacked rectangles or tapered thin rectangles (FIG. 5D 560). Other relative projection shapes may include but should not be limited to spheroid, sphere, sphere on cylinder, sphere on pyramid, sphere on cone, cone, cylinder, pyramid, and polyhedron. Whatever variety of tip shape is chosen, the customary overall composite tip width can vary between 2 mm and 20 mm, most preferably between 8 mm and 12 mm while the thickness may vary between 0.5 mm and 4 mm, most preferably 1-2 mm. Adjacent the tip, but possibly incorporated into the tip, is the planar-tissue-altering-window/zone 540. In the relative recessions of the tip is the electrically conductive tissue lysing element 565 (usually hidden from view at most angles) which may have any geometric shape including a thin cylindrical wire. The electrically conductive lysing element can be in the shape of a plate or plane or wire and made of any metal or alloy that does not melt under operating conditions or give off toxic residua; optimal materials may include but are not limited to steel, nickel, alloys, palladium, gold, tungsten, copper, and platinum. These metals can become oxidized thus impeding electrical flow and function. Calculated oxidation of the electrically conductive lysing elements may be used to plan obsolescence so that one embodiment of the device may be a low cost, disposable, one-time-use device. However, other embodiments intended for multiple use require the tip's electrically conductive tissue lysing elements be protected or coated with materials that include but are not limited to Silverglide™ non-stick surgical coating, platinum, palladium, gold and rhodium. Varying the amount of protective coating allows for embodiments of varying potential for obsolescence capable of either prolonging or shortening instrument life. The electrically conductive lysing element portion of the tip may arise from a plane or plate of varying shapes derived from the aforementioned materials by methods known in the manufacturing art, including but not limited to cutting, stamping, pouring, molding, filing and sanding. This electrically conductive lysing element plate 565 may be an insert attached to a conductive element in the shaft or continuous with a formed conductive element coursing all or part of the shaft. An electrically conductive element or wiring 580 brings RF electrosurgical energy down the shaft to electrically conductive lysing elements associated in part with the recessions. The electrically conductive element or wiring may be bifurcated to employ hand switching if an optional finger switch is located on handle; the electrically conductive element or wiring leading from the shaft into the handle may be bundled with other leads or energy delivering cables, wiring and the like and exit the proximal handle as insulated general wiring to various generators (including electrosurgical), central processing units, lasers and other sources as have been described herein. The plate may be sharpened or scalloped or made to slightly extend outwardly from the tip recessions into which the plate will fit. Alternatively, since cutting or electrical current can cause an effect at a distance without contact the electrically conductive lysing element may be recessed into the relative recession or flush with it. Adjustable, locations of the electrically conductive lysing element with respect to the relative recession may be achieved by diminutive screws or ratchets. The plate, which is most desirably between 0.01 mm and 1 mm thick, can be sharpened to varying degrees on its forward facing surface. Plate sharpness may increase the efficiency with which electricity will pass from the edge cutting the target tissue. However, proper function even when variably dull or unsharpened may be unhampered since electrosurgical cutting current immaterially cuts beyond the electroconductive edge by a distance of usually between 0 and 1 mm. Plate sharpness may be a disadvantage in determining whether a tip lysing conductor portion is too oxidized to function efficiently because scalpel like cutting may allow passage of the instrument but likely may also lead to increased bleeding when electrical cutting current is absent. Because standard operating forward motion of the invention's tip exposes it to relatively cooler tissue fluid temperatures, the heat of operation at the tip the electrosurgical tissue lysing conductor should not reach temperatures that will unseat it for significant operating times, however under relatively "dry" conditions or protracted usage periods, secondary and tertiary methods of insulation at the junctions between the tip proper and the electrosurgical tissue lysing conductor may be needed to prevent melting at the tip and unseating. For example, thin ceramic coatings of under one-one hundredth of an inch thick may be epoxy bonded to the surface of the electrosurgical lysing conductor plate in all but the points of tissue exposure, the ceramic coating may further be coated with (but not all-inclusively) olefins, Halar® (monochlorotrifluoroethylene that may soften near 550° C.), Teflon® (tetrafluoroethylene that may soften near 750° C.), FEP (fluoronated ethylene polypropylene, HMWPE (high molecular weigh polyethylene) or epoxy by methods Vitek Corp., Derby, Conn. Plates singly or doubly insulated in this manner may then be seated into an appropriately matched recipient tip structure with less risk of melting following prolonged operating discharge. The electrically conductive lysing element may also exist in the shape of a simple wire of 0.01 mm to 3 mm, preferably between 0.1 mm and 1 mm, and be uncoated or coated with the aforementioned similar materials to prevent oxidation or modify obsolescence. The wire may be singly or doubly insulated as was described for the plate and may have the same electrical continuities as was discussed for the planar (plate) version. The preferred electrosurgical current for the electrically conductive lysing element is of the monopolar "cutting" variety and setting and may be delivered to the tip lysing conductor in preferably a continuous fashion but optionally a pulsed fashion as well. The surgeon can control the presence of current by a foot pedal control of the electrosurgical generator or by button control on the shaft (forward facing button). The amount of cutting current can be modified by standard interfaces or dials on the electrosurgical generator. The tip current can be further pulsed at varying rates by interpolating gating circuitry at some point external to the electrosurgical generator by standard mechanisms known in the art preferably at rates of 1 per second to 60 per second. For most of the combination embodiments, for the electrically conductive lysing element is a monopolar tip in contact with conductive elements in the shaft leading to externald surgical cable leading to an electrosurgical generator from which emanates a grounding or dispersive plate which is to be placed elsewhere in contact with the patient's skin, preferably the thigh. Such circuitry is controlled and gated/wired from the cutting current delivery system of the electrosurgical generator. Acceptable Valleylab electrosurgical generators include ValleyLab Force 1B with maximum P-P voltage of 2400 on "cut" with a rated load of 300 Ohms and a maximum power of 200 Watts, maximum P-P voltage of 5000 on "coagulate" with a rated load of 300 Ohms and a maximum power of 75 Watts; ValleyLab Force 4 has a maximum P-P voltage of 2500 on "cut" with a rated load of 300 Ohms and a maximum power of 300 Watts, 750 kHz sinusoidal waveform output, maximum P-P voltage of 9000 on "coagulate" with a rated load of 300 Ohms and a maximum power of 120 Watts using a 750 kHz damped sinusoidal with a repetition frequency of 31 kHz. The tip may also be manufactured from multilayer wafer substrates comprised of bonded conductive strips and ceramics; conductive materials include those already described for tip manufacture. Some tip embodiments, when viewed only from the top display recessions flush with protrusions, however at some other viewing angle the difference become apparent. In an alternative embodiment, the electrically conductive lysing elements may be bifurcated or divided into even numbers at the relative recessions, insulated and energized by wiring to an even number of leads in a bipolar fashion and connected to the bipolar outlets of the aforementioned electrosurgical generators. Rings partly or completely encircling the shaft of the hand unit can be linked to a partner bipolar electrode at the tip or on the tissue-altering-window/zone. Such bipolar versions will decrease the available power to electrically modify certain tissues, especially the thickest.

Figure 5C:
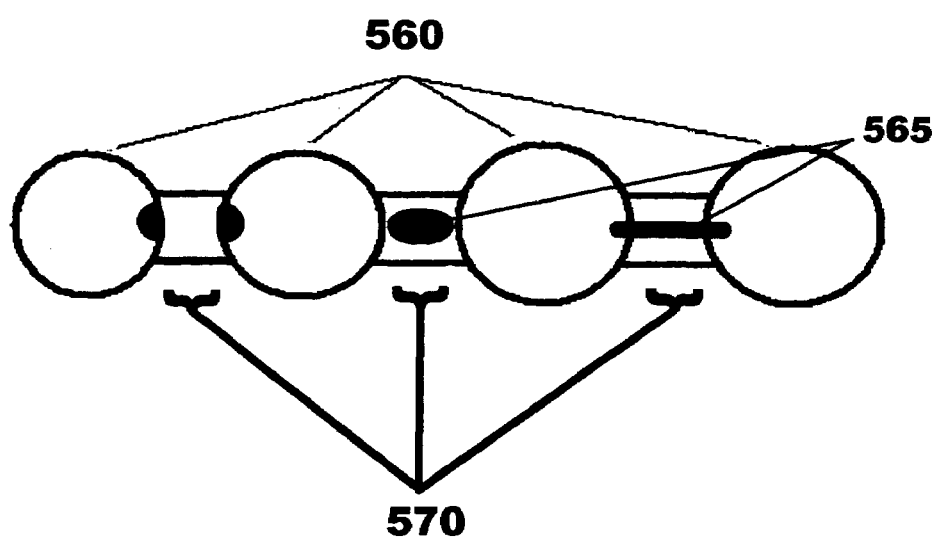
FIG. 5C is a frontal view of the tip area of the apparatus with a focus on relative protrusions, relative recessions and associated energized segments.
Figure 5D:
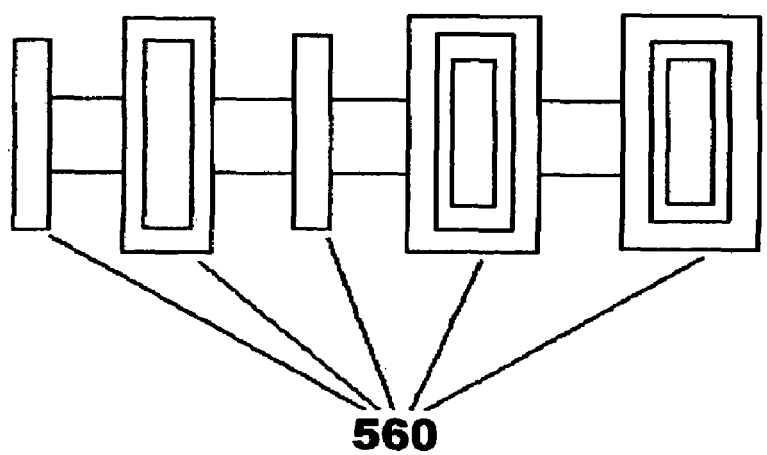
FIG. 5D Front view of tip showing various relative protrusions includes a wide variety of geometric shapes such as stacked rectangles or tapered thin rectangles.

FIG. 5C is a front view of the tip of the face-lift apparatus. The tip has four protrusions 560 now seen as ovals and three recessions 570 now seen as thinned lines which contain seated electrically conductive elements 565. Note the relatively oval shaped-protrusions in seen from this angle. Regarding the nomenclature used to describe bulbs and lysis, relative protrusions and relative recessions, protected and exposed, in this and copending applications: relative protrusions are usually exposed and probe-like and bulbous; relative recessions are protected areas and capable of lysing tissue. We would classify any design that shows a relative protrusion or relative recession from at least one angle of viewing to represent a protrusion or recession and fit the description of this device. Tip protrusion shapes can include a wide variety of geometric shapes especially those that facilitate smooth instrument passage and maintain adequate spacing from the firm dermal layer. In an alternative embodiment, the tip or distal shaft is made of metal that is electrically insulated at all points, excluding the relative recession(s), and excluding the contact points for leads from the energy source; this allows for electrosurgical energy passage at the areas of the energized lysing segments.

FIG. 5D. Front view of tip showing various shapes of relative protrusions 560 including but not limited to a wide variety of round or geometric shapes such as ovals, stacked rectangles or tapered thin rectangles.

FIG. 5E Alternatively, since cutting or electrical current can cause an effect at a distance without contact the electro-conducting tissue lysing element (dashed lines indicate difficult to view) may be recessed into 571 the relative recession 570 or flush 572 with it. The difference between the relative recessions may vary 0.001 mm to 10 mm in depth with respect to the relative protrusions when viewed from the top. Also shown for comparison is an electroconductive lysing element that is projecting slightly 573 from the relative recession.

Figure 5F:
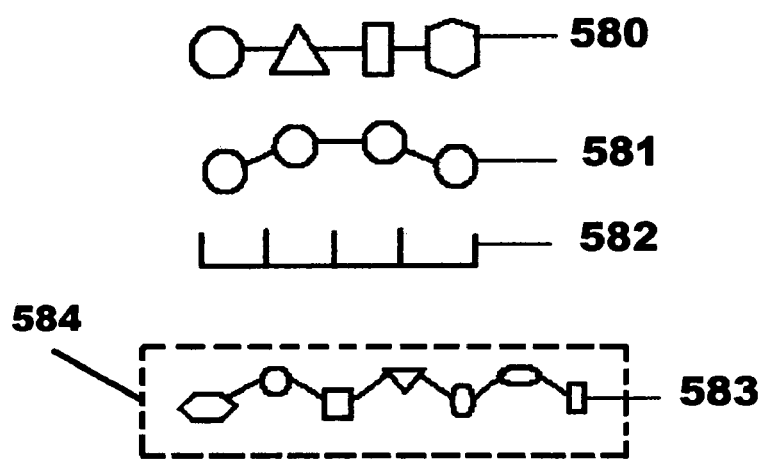
FIG. 5F is a front view of the tip showing the substantially planar alignment of the relative protrusions and relative recessions. A range of potential embodiments take place within a rectangular field (left to right): completely planar, "Barbershop" tip, curviform, geometric. Also shown are a variety of physical contact relationships between the relative recessions and relative protrusions including (left to right): bottom junctions, below junctions, angulate junctions.

FIG. 5F The alignment of the relative protrusions and relative recessions is substantially planar and thus may include embodiments that are completely planar 580 or those with some arc, or curvature 581 or even geometric 583 within a substantially planar range indicated by the dashed rectangle 584. Also shown is the "Barber-shop" embodiment 582 of the tip in which the rectangles become infinitely thin in a direction perpendicular to a line through the axis of the ends of the protrusions. Additional embodiments include but are not intended to be limited to those in which the plane of the relative recessions is not located within the plane passing through the horizontal center of the relative protrusions. Instead the relative recession plane may be located below 582 or at some other extreme point relative to the horizontal plane through the relative protrusion. Altered positioning will effect the depth of lysing and amount of intraoperative and postoperative bleeding as well as dermal plexus damage.

Figure 6A:
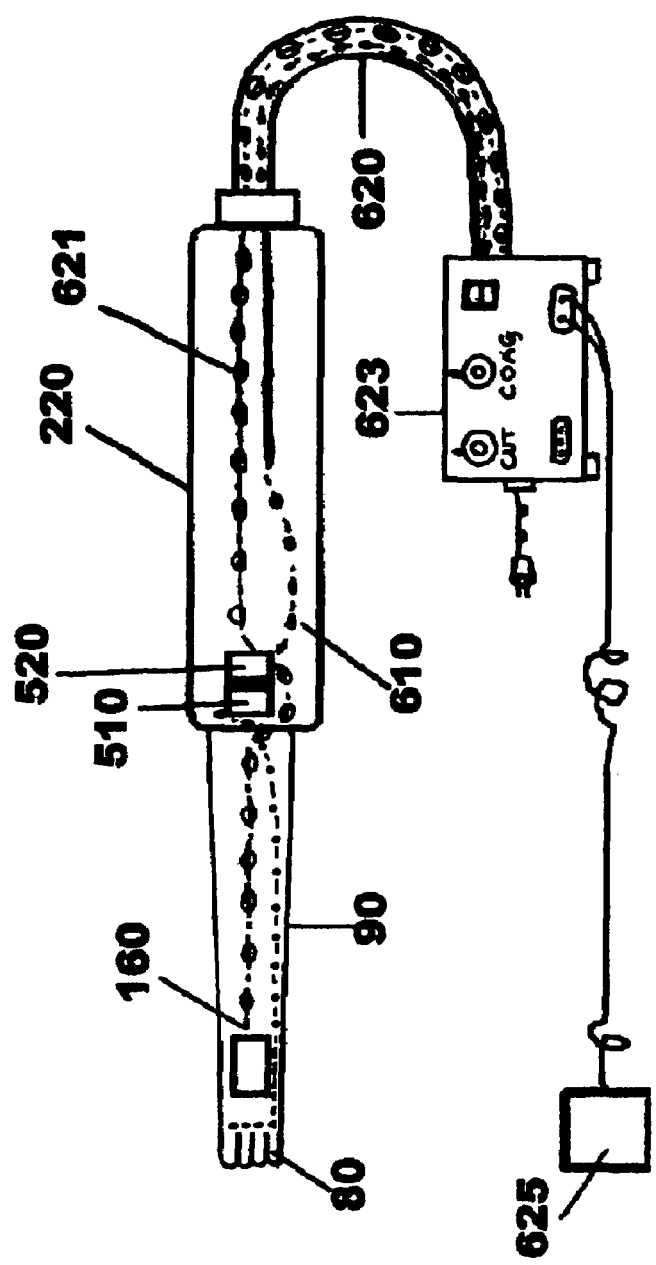
FIG. 6A is a top view of electrosurgical embodiment of tip, shaft, handle and relative location of the planar-tissue-altering-window/zone.

FIG. 6A is a top view of an internal schematic of the tip 80, shaft 90, handle 220 of an electrosurgical embodiment of the planar-tissue-altering-window/zone 160. Wire bundle containing conductive element 610 leading to switch attached to "cut" (cutting current) control button 510 which then leads to lysing tip inserts comprised of at least electrically conductive lysing elements. Wire bundle also contains other leads that pass through handle and shaft as well as single, grouped or arrays of optional tip thermal and impedance sensors. An output device interposed along leads connected to sensors is located somewhere outside the handle and may display the temperature in Centigrade or elicit feedback control through a CPU. Other sensors such as impedance sensors may follow a similar path and read-out (Ohms) with feedback inhibition. For the microwave radiofrequency or monopolar radiofrequency electrosurgical window/zone embodiment, also passing through wire bundle 620 outside the shaft, is conductive element (which is bifurcated if it optionally leads to control switch attached to "coag" (coagulate current) control button 520) that eventually leads to energetic element at planar-tissue-altering-window/zone. Footswitch control or voice activated control for the planar-tissue-altering-window/zone would be convenient since the operating surgeon's hand may be occupied with device motion and activation of the electrosurgical tissue lysing conductor.

Figure 6B:
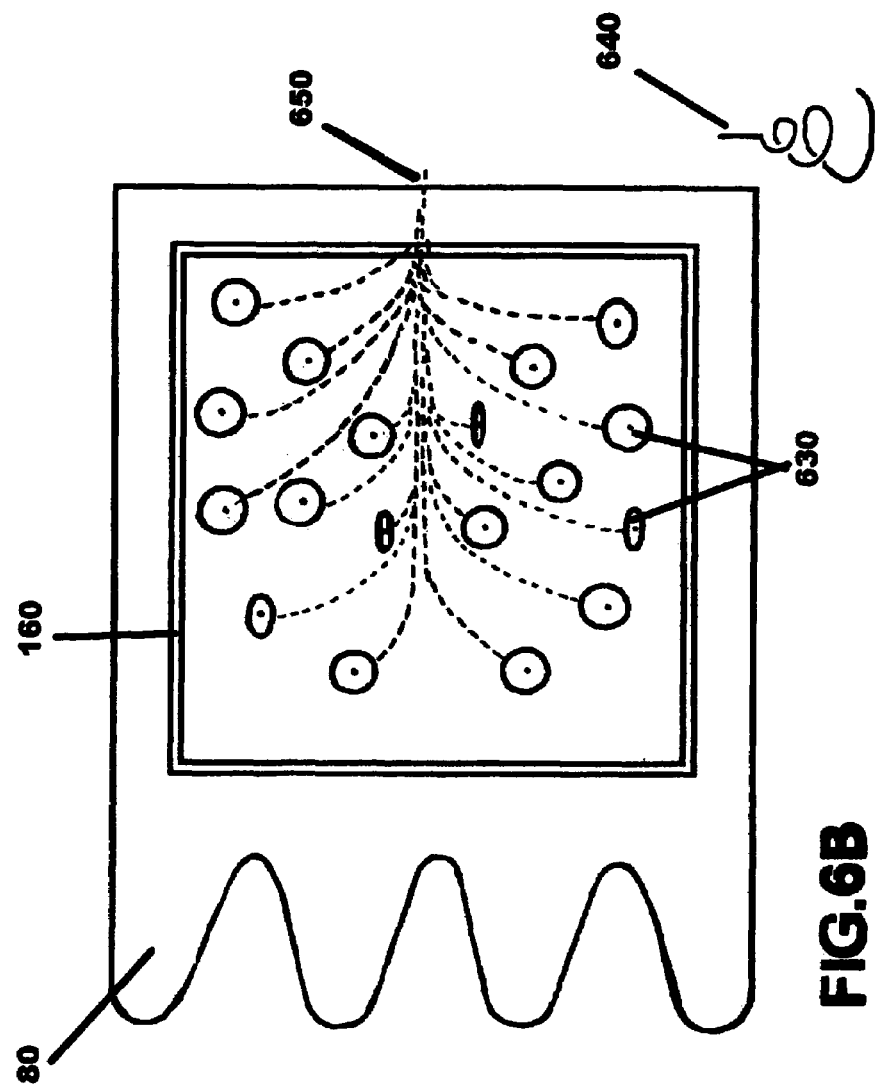
FIG. 6B is an enlarged plan or top view of an electrosurgical embodiment with a focus upon the components and major leads to the planar-tissue-altering-window/zone. Also shown are various geometries for electroconductive tissue denaturing termini (left to right): cone, pyramid, round, geometric, bristle, bristle on spring, bristle with "frizzies".

FIG. 6B is an enlarged plan or top view of an electrosurgical embodiment of the tip 80 and adjacent planar-tissue-altering-window/zone 160. Scattered about said zone are one or many more electroconductive tissue denaturing termini 630. Preferably between six and twenty termini are present. Said electroconductive tissue denaturing termini may be scattered randomly throughout the planar-tissue-altering-window/zone or may be arranged in patterns. Said electroconductive tissue denaturing termini may be formed in various shapes and possess varying degrees of insulation on various aspects of their geometry and be present in numbers between 1 and thousands. In one preferred embodiment said electroconductive tissue denaturing termini are shaped as pointed cones 630 with their bases embedded or counter-sunk in the planar-tissue-altering-window/zone. Other geometrical embodiments include but are not limited to cube shaped, pyramid shaped, hemispherical, sphere shaped with cylindrical attachment area, and cylinder shaped. Insulation may be placd covering between 0 and 100% of the contact surface of the termini. The "ladybug" is a dome shaped termini embodiment covered with insulation containing numerous <0.1 mm holes. Other tertiary shapes may include but are not limited to straight bristle shaped, bent bristle shaped, bristle shaped atop a cone, bristle shaped distally atop spring shape proximally -640-, and bristle shapes with further branched bifurcation or "frizzies". The electroconductive tissue denaturing termini may be made any electroconductor or any metal or alloy that does not melt at operating temperatures or give off toxic residua; optimal materials may include but are not limited to steel, nickel, gold, tungsten, copper, alloys and platinum. Various metals can become oxidized thus impeding electrical flow and function. Calculated oxidation of said termini may be used to plan obsolescence so that one embodiment of the device may be a low cost, disposable, one-time-use device. However, other embodiments intended for multiple uses require said termini to be protected or coated with materials that include but are not limited to Silverglide™ non-stick surgical coating, platinum, palladium, gold and rhodium. Varying the amount of protective coating on the termini allows for embodiments of varying degrees of obsolescence that may either prolong and shorten instrument life. Planar-tissue-altering-window/zone and electroconductive tissue denaturing termini may be formed as multilayer wafer substrates comprised of bonded conductive strips, ceramics, plastics, silicon, glass, glass/ceramics and materials using annealing techniques known in the art. Carbon, graphite, and graphite-fiberglass composites are also potentially useful. Said planar-tissue-altering-window/zone (that seats electroconductive tissue denaturing termini) may be constructed at least partially of materials that are both electrically non-conductive and of low thermal conductivity; such materials may include but are not limited to: porcelain, ceramics, glass-ceramics, plastics, varieties of Teflon® and other such materials mentioned herein. Multilayer ceramic electrodes are also commercially available from VisPro Corp. of Beaverton, Oreg. Additionally, said planar-tissue-altering-window/zone may be constructed of a support matrix of suitable insulating material (e.g., ceramic or glass material such as alumina, zirconia: Kyocera Industrial Ceramics Corporation, Elkgrove, Ill.). Sealing material for a ceramic embodiment should have a compatible thermal expansion coefficient and a melting point different from that of platinum or titanium and alumina or zirconia, typically being a glass or ceramic. A favored ceramic for construction is Forsterite of 2.9 g/cm3 density, flexural strength of 1500/kg/sqcm, temperature expansion coefficient (83+/−5)10E-7, composition: $Al_2O_3$ 0.8%, $SiO_2$ 41.7%, MgO 51.5%, BaO 6%. Another favored ceramic for construction is BK 94-1 (Russian Index), flexural strength of 3200/kg/sqcm, composition: $Al_2O_3$ 94.4%, $SiO_2$ 2.8%, $MnO_2$ 2.3%, $Cr_2O_3$ 0.5%. Depending upon the desired longevity and the potential for the energy passage from the termini to create temperatures that may be near the softening point of such encasements as tetrafluoroethylene, secondary and tertiary methods of insulation of the junction between the termini and materials that may soften may be needed to prevent unseating. For example, thin ceramic coatings of under one-one hundredth of an inch thick may be epoxy bonded to the undersurface of the termini in all but the points of electrically conductive element or wiring contact; the ceramic coating may further be coated with materials such as olefins, Halar®, Teflon®, FEP or epoxies. Termini singly or doubly insulated in this manner may then be seated into a window/zone comprised of aforementioned materials. An electrically conductive element or wiring 650 brings RF electrosurgical energy from the shaft and electrosurgical generator to the electroconductive tissue denaturing termini mounted in the planar-tissue-altering-window/zone. Heating derived from the high frequency voltage differential existing between electrodes and the grounding plate results in temporary and permanent contraction of the surrounding tissues, especially fibrous containing ones. Desirable results do not necessitate total cell necrosis, only partial denaturing can cause tightening. This embodiment's source of current from the electrosurgical generator is usually monopolar "Coag" or coagulation mode thus requiring a grounding plate be applied to a distant location on the patient's skin, however desired electrosurgical generator current for other embodiments may lie on the spectrum of a "blend" setting or more than a pure cutting "cut" setting. The surgeon can control the presence or absence of current by a foot pedal control of the electrosurgical generator or by button control on the shaft and the level of cutting current can be controlled by standard interfaces or dials on the electrosurgical generator. The window/zone current can be further pulsed at higher rates by interpolating gating circuitry at a point external to the electrosurgical generator by standard mechanisms known in the art at rates including but not limited to 1 per second to 200 per second. Pulsing this embodiment would leave an organized or random pattern (spotty) of injury to the target tissues with the optimal choice being a pulsed rate and energy level that provides for clinically unrecognizable minute subsurface areas of damage (fractiles) that induce neighboring tissues to contract in a pleasing fashion. In an alternative unipolar embodiment, the electroconductive tissue denaturing termini mounted in the planar-tissue-altering-window/zone may be grouped or divided and wired using techniques standard in electrical engineering to fire in a random pattern, or such a way that the firing of said termini 5 as the instrument is moved provides for a nonuniform or spotty pattern of electrosurgical tissue alteration or spotty tissue destruction. In an alternative embodiment, the electroconductive tissue denaturing termini mounted in the planar-tissue-altering-window/zone may be grouped and divided or divided into even numbers, insulated from the opposite electronic pair and energized by wiring to an even number of leads in a bipolar 10 fashion and connected to the bipolar outlets of the aforementioned electrosurgical generators. Another alternative bipolar embodiment involves placing one or more metal rings around the shaft as the return or second electrode in a pair with one or more the electroconductive tissue denaturing termini acting as the first. Such bipolar versions are weaker and lack sufficient power to electrically modify the thickest tissues when compared to monopolar versions. Energy availability may be more problematic when trying to energize or denature the subcutaneous fatty layer upon turning the instrument over following the initial plane forming passes while trying to precisely "cook the fat" below to get overlying skin contraction. Traumatizing the subcutaneous tissue or "cooking the fat," causes inflammation in the subcutaneous layer which transfers to over-draping dermal flap causing dermal inflammation and thus contraction (unpublished, preparing manuscript to be submitted to medical journal). Likewise, traumatizing muscle (in this case the platysma muscle that envelopes most of the front of the neck) to cause char or other debris, may cause a similar contractile response in the platysma and the over-draping dermal skin flap. The formation of carbon and carbonized organic chemicals (matter) likely induces inflammation via several pathways including: bringing macrophages which have to envelope and digest the material and by inducing leakage of cellular mediators which inflammatory cell gatherings and their resultant tissue cascade and tissue modifications. Alternatively, plurality of substantially planar-tissue-altering-window/zones can be present at multiple locations on the shaft, however more proximal locations will not "see" as much target tissue surface area to energize as distal ones because the handle cannot fit into the incision. Furthermore, those multiple possible locations on the shaft of substantially planar-tissue-altering-window/zones include placing the window/zone on the bottom or opposite side of customary use. Zones can be present on both sides of the shaft, for simultaneous energy or matter transfer.

FIG. 6A also describes a typical operating room equipment set up connected to the shaft and handle 220 for the monopolar radiofrequency electrosurgical planar-tissue-altering-window/zone embodiment. Passing through wire bundle, is conductive wire 621 leading to switch 520 attached to "coag" (coagulate current) control button further leading to energetic element at planar-tissue-altering-window/zone. Said circuit originates from the "coagulation" controlling and delivering ports of high frequency electrosurgical generators—such as a Valleylab Surgistat or Force 1. From separate or similar electrosurgical generators wire bundle contains conductive element 610 leading to switch attached to "cut" (cutting current) control button 510 that further leads to electrically conductive lysing elements. The patient is grounded to both machines using disposable grounding gel plates 20 as dispersive electrodes 625. Depending upon the patient's skin type, it may be possible that using only the current applied to the plexus protecting tip and its attached electrosurgical tissue lysing conductor the surgeon can electro-modify the dermal tissues to the point that cosmetically acceptable tightening and strengthening occur. Thus, in some cases (thin skin, age, heredity, etc.) it may not be necessary to use any type of energy from the planar-tissue-altering-window/zone if simple energy from the cutting tip can cause significant enough tissue contraction, damage and alteration. Although the planar-tissue-altering-window/zone is customarily placed on the side of the shaft meant to face superiorly, a separate planar-tissue-altering-window/zone may be located on the opposite side of the shaft using any form of window/zone emanating energy described in this or related applications.

Figure 7:
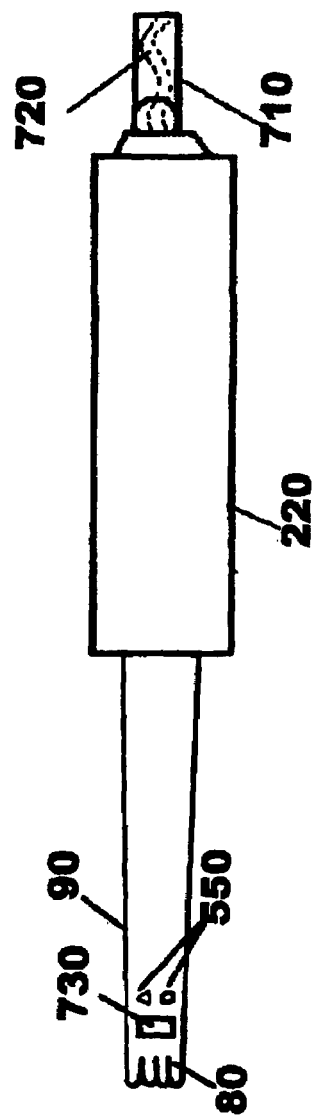
FIG. 7 is a top view of LASER embodiment of tip, shaft, handle and relative location of the planar-tissue-altering-window/zone.

FIG. 7 is an enlarged plan or top view of the macro and microfractile coherent electromagnetic light (LASER)/non-coherent electromagnetic (light) planar-tissue-altering-window/zone embodiment existing in the same instrument as previously described tip 80, shaft 90 and handle 220. Passing into shaft and adjacent to or formed into external bundle, are multiple or single fiberoptic elements 720 leading to planar-tissue-altering-window/zone 730. The energy passing through the fiberoptic is controlled at the electromagnetic energy source by footswitch. In one embodiment, the planar-tissue-altering-window/zone is an optical window 730 that allows laser light to exit the shaft and irradiate nearby target tissue. A light delivery means which can be a hollow waveguide or single or multiple optical fibers (such as metal-coated plastic manufactured by Polymicro Technologies, Inc of Phoenix, Ariz.) is contained in external conduit 710. The external conduit can also be an articulating arm as is commonly used in surgical laser systems. Additional control wires and power may be delivered to the handpiece via the external conduit. However, using footpedal control from electromagnetic energy radiation source or control interface, dial, or panel will likely be less cumbersome for the surgeon and reduce the expense of handpiece finger-control manufacture. Optional window 730, possibly made of Germanium, allows egress of laser light and collection of data by thermal sensors 550, may be of varying size. In another embodiment, a multiplicity of optical fibers may terminate at specific or random places within the planar-tissue-altering-window/zone. Such bare or coated fiberoptic termini may protrude from, be flush with or be recessed into materials comprising the planar-tissue-altering-window/zone. Bare fiberoptics that are ethylene oxide sterilizable may be seated in a thermally nonconductive background, preferably at uniform 90 degree angles, but variable angles between 0 and 180 degrees may also be efficacious. The preferred light delivery means depends on the wavelength of the laser used. Infrared light emitted by the heated tissue can also be collected through the window and sensed by an infrared detector to measure the tissue temperature. For $CO_2$ laser irradiance, reliable sources include standard operating room units such as the Encore Ultrapulse® from Lumenis Corp. of Santa Clara, Calif. is capable of providing continuous $CO_2$ laser energy outputs of 2-22 mJoules at 1-60 Watts, older models of the Coherent Ultrapulse are suitable (Coherent now owned by Lumenis). The hollow section of shaft may act as a waveguide or may contain a metal-coated plastic fiberoptic or waveguide to allow laser light to pass through and exit from window near tip. The window allows egress for laser light delivered to apparatus. Lasers usable in the present invention include both pulsed and continuous wave lasers such as $CO_2$, erbium YAG, Nd:YAG and Yf:YAG. The beam diameter can be changed in standard manners by those skilled in the art. However, this list is not intended to be self-limiting and other wavelength lasers may be used. The coherent or noncoherent radiation can be delivered from their source by articulating arm or fiberoptic (as the case of the wavelength may be) and enter the handpiece and be further directed to the planar-tissue-altering-window/zone via waveguide and mirror or fiberoptic terminating at a mirror or fiberoptic terminating internally within, flush with, or externally from, materials comprising the planar-tissue-altering-window/zone. One embodiment to produce larger macro-fractile-like areas of target tissue denaturation is to split such LASER energy as $CO_2$ into multiple smaller fiberoptics in the range of 0.1 mm to 1 mm in diameter $CO_2$ laser carrying optical fiber manufactured by Polymicro Technologies, Inc of Phoenix, Ariz. Said fiberoptics may terminate axially or at some angle adjacent to a mirror directing radiation to planar-tissue-altering-window/zone so that LASER energy emanates from the window into the target tissue. Said fiberoptics may terminate protruding from, flush with or recessed in base materials comprising the planar-tissue-altering-window/zone. Said window/zone may be homogenous with or materially similar to the rest of the shaft or annealed in to it using methods similar to those described for the electrosurgical embodiment of the planar-tissue-altering-window/zone. Lower melting temperature plastics may also be suited to seat said fiberoptics into the planar-tissue-altering-window/zone. Fewer but larger fiberoptics on the order of 1 mm like those manufactured by Polymicro Technologies may be used to create larger areas of controlled focal necrosis of the target tissues in the mid and lower dermis. Desirable sizes of tissue destruction of under 1 mm with interposed areas of sparing of the vascular supply help avoid confluences of altered tissue and reduce clinically visible scarification seen on close inspection or at social distances. Assuming forward motion in the target tissue of 1 cm/sec of the planar-tissue-altering-window/zone, LASER pulse frequencies in the range of 1-1000 pulses/second with three or more fiberoptic termini (preferable arrays include 10 larger diameter fiberoptic termini) would bring about clinically acceptable but sufficiently small local areas of controlled focal necrosis of the target tissues. Overly intense nonpulsed continuous electromagnetic radiation may streak by tissues in an uninterrupted fashion isolating larger areas of tissue from access to fresh oxygenated blood. Less intense nonpulsed electromagnetic radiation may bring about some cellular contractile response without damage to the blood vessels. To deliver microfractiles of energy internally the handpiece may be fitted with a mirror adjacent to the planar-tissue-altering-window/zone such that when an adapted laser light source (Reliant MTZ™SR Laser, Reliant Technologies, Palo Alto, Calif.) is altered in its focal length and fitted to the proximal end of the handle of the embodiment, random or patterned LASER may be transmitted down the handpiece and shaft onto the mirror and redirected out the window in the planar-tissue-altering-window/zone onto the target tissues. A range of settings for internal use may exist, however preferred settings are in excess of those externally applied by the 15 micron unit of 32 J/sqcm. Because of the thickness of the lower dermis and attached subcutaneous greater energy will be needed when lasing from inside out to produce Microscopic Necrotic Debris within the dermis leading toward the upper dermis while avoiding damage to the epidermis. Tissue impedance and thermal monitoring devices similar to those described with the electrosurgical window may be used in conjunction with LASER energy window/zone devices.

Figure 8:
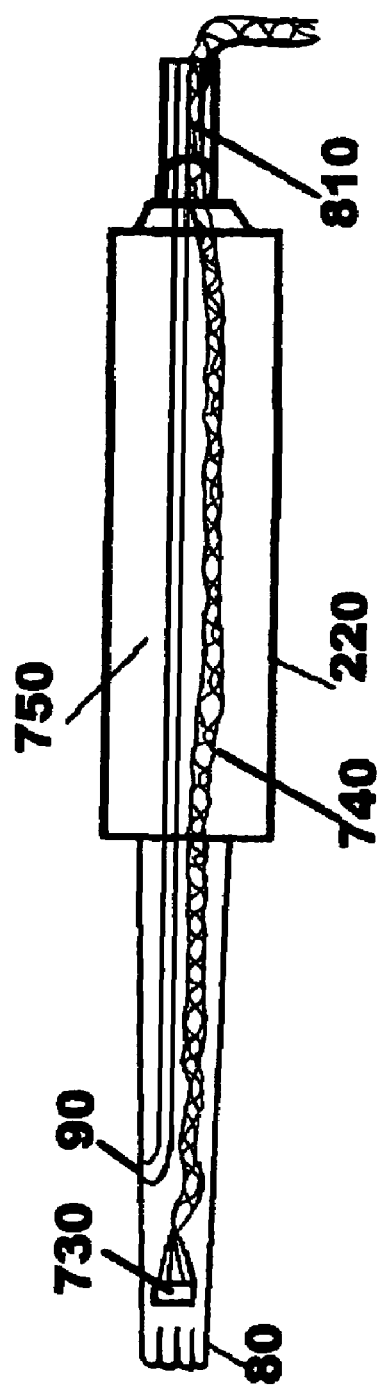
FIG. 8 is a top view of tip, shaft, handle and relative location of the planar-tissue-altering-window/zone for transferring other forms of energy, and matter onto target tissue.

FIG. 8 is a top view of an internal schematic of the handle 220, shaft 90, and tip 80 leading to planar-tissue-altering-window/zone 730 capable of delivering various forms of energy to target tissue. Coursing the handle and shaft are fiberoptics, wiring, conductive elements, evacuation tubing, insulated gas or fluid-transmitting tubing, monitoring leads and any other control and monitoring connections. Optional thermal and impedance sensors may exist in or on the shaft or tip. Planar-tissue-altering-window/zone embodiments for intense pulsed light emission may be constructed as in co-pending applications and as follows. In intense pulsed a non-coherent, nonLASER, filtered flashlamp emits a broadband of visible light. The flashlamp, such as a smaller version of that used by ESC/Sharplan, Norwood, Mass. (500-1200 nm emission range; 50 J/sqcm fluence; 4 ms pulse; 550 nm filter) may occupy the handle or window/zone of the embodiment. Should IPL flashlamp accommodations increase shaft thickness significantly, the 1 cm entrance incisions can be easily transformed into 1.5 cm incisions along the anatomic lines and combined with a perpendicular incision of 1-1.5 cm to form a small A to T flap from which a much larger diameter shaft can enter yet be easy to sew. The flashlamp emits optical and thermal radiation that can directly exit the planar-tissue-altering-window/zone or be reflected off a reflector to also exit through window. The reflector can have a parabolic shape to effectively collect all radiation emitted away from the window which can be made of a wide variety of glass that transmits optical, near infrared and infrared light (e.g., quartz, fused silica and germanium.) Emission spectra can be filtered to achieve the desired effects. Thermal emissions or visible radiation absorption may locally heat the dermis to alter collagen; thermal sensors control reduces overheating. In order to eliminate excessive heating of the shaft and the surrounding facial tissue, the flashlamp and reflector are thermally isolated by low thermal conductivity materials or cold nitrogen gas can be pumped through a hollow in the shaft or handle. The handle can be an alternate location for the so that emitted radiation may be reflected by a mirror through the window/zone. A planar-tissue-altering-window/zone embodiment for radiofrequency microwave emission may also be constructed as in co-pending applications; in such an embodiment the shaft may be made of metal or plastic or ceramic connected to a plastic or polymer or ceramic tip section that has an even total number of phased array antennas attached or exposed on a planar or relatively planar or slightly curviform side. The phased array of antennas is made of metal (preferably stainless steel, aluminum, gold, steel, or platinum). The phased array is able to function in the range of 1 to 10 gigahertz yielding up to 20 watts of power with a depth of penetration of 1-3 mm. A cryotherapy embodiment of the planar-tissue-altering-window/zone -730-, utilizes plastic or thermal resistant tubes or tubules 740 on the order of 0.01 cm to 1 cm to transmit cryotherapy agents via the inert or insulated tubing 810. In the cryotherapy embodiment, a cold inert gas or liquid such as nitrogen (196° C.) is suitable for one embodiment and maintained in a cryogenic container or reservoir located outside the shaft and gated nearby there. Cryotherapy agents change, alter, damage or modify targeted tissues not in the freezing (preserving phase) but in the thawing phase in which thermal energy, derived from the surrounding internal and external human environment heats the now-thawing target tissues causing damage including but not limited to intracellular disruption of organelles, cellular membrane lysis, crystallization, and matter precipitation. A side benefit of nitrogen is stability and inhibition of combustion from nearby operating electrosurgical or electromagnetic devices. The density compares with the cooling capability of liquid nitrogen and is about one thousand times that of nitrogen gas. Nitrogen, in its liquid form, is more difficult to transport from the reservoir to the window without significant thicknesses of insulation. Therefore gas, and mixtures of gas and fluid containing mostly gas would be easier to control while maintaining convenient handpiece size. 1 cc of cold nitrogen gas at "window" temperatures varying from −196 to −30° Centigrade passing at an emissions rate of between 1 cc/0.1 sec to 10 seconds may be coordinated by thermal sensor feedback loop release to more precisely alter target tissues depending upon target tissue temperature and density at time of cryotherapy. Released gasses or fluids that would vaporize to sufficient volumes of gas into the relatively closed cavity between the lysed tissue planes may inflate the face necessitating the use of evacuation tubing or conduits to release gas build-up and pressure 750. Footswitch control or voice activated control (in addition to optional thermal sensor/CPU feedback loops) of fluid release would be convenient since the operating surgeon's hand may be occupied with device motion or activation of the lysing function.

Direct piezoelectric versions of the tissue-altering-window/zone may impart vibrational energy to water molecules contained in target tissues passing adjacent to the piezo. Temperature elevations cause collagenous change and cell wall damage, however ultrasonic energy application may have disruptive effects at the subcellular level as well. Crystals that acquire a charge when compressed, twisted or distorted are piezoelectric. Electrical oscillations applied to certain ceramic wafers cause ultrasonic mechanical vibrations. Energy output for piezoelectric window/zones should range from 1-30 J, with a preferred range of 1-6 J in a surgical device moving about 1 cm/second. As with all other embodiments, temperature and impedance sensors providing intraoperative real-time data can modulate energy input into the piezoelectric which is energized by conductive element in shaft in further connection with control unit and power supply. In yet another embodiment, hot gasses or liquids or combinations thereof may be sprayed from the window/zone onto the target tissues. For example, collagen denatures at 70° C. and cellular damage builds, steam or hot water can be delivered by a variety of mechanisms to exit the window/zone onto the target tissues. Steam under pressure can be delivered via insulated, high-pressure thermal-resistant line from an auxiliary water heating device outside of the shaft or handle. The line may divide into one or more tubules before delivery to the target tissues; a suction lumen may remove any excess pressure built as a result of gaseous emissions within the relatively closed space. Alternatively, steam may be produced by minute individual piezoelectrics located in the window/zone. In this embodiment, small tubules deliver a liquid capable of being vaporized within the temperature range that the small piezoelectrics function, such piezoelectrics are currently in use for painting and ink application (MicroFab Tech Inc, Royal Cox, Plano, Tex.). Water is delivered to the piezoelectric and retrograde motion is prevented by a unidirectional microfluidic flow valve system. Piezoelectrics, numbering between 1 and 1,000, may be mounted in an array in the window/zone, with microfluidics flow valves preventing retrograde motion of water in the water depositing flow system. Randomly or non-randomly, various piezoelectrics may be controllably made to impart vibrational energy to water molecules to make localized areas of steam. Steam may be ejected from Teflon® or similar tubing in a spotty or uniform fashion to modify or traumatize tissues on either side of the facial dissection plane.

The prolotherapy embodiment of the planar-tissue-altering-window/zone provides instillation of hypertonic glucose (D-glucose), sodium morrhuate, and phenol and other fibrosis-inducing chemicals or mixtures in liquid, foam, suspension, powder, or any other form known to possess the ability to controllably traumatize tissue or stimulate fibroblasts or increase collagenization (including but not limited to concentrated salt solutions, acids, bases, detergents, sodium deoxycholate, polidocanol, sodium docecyl sulfate, and hypertonic saline) in the cavity of the tissue plane formed by the lysing action of the invention. If acids or bases are used to deliberately traumatize tissue to induce fibrosis then they may be neutralized by their opposing party for example an acid solution induces trauma and is neutralized by a dilute sodium bicarbonate lavage. Non-solutions that can irritate or controllably traumatize human tissues into a fibroblast/collagen response could include, but should not be limited to, silicone/saline suspensions, collagen suspensions, fat globule/oil 10 water suspension, sand, glass, carbon and carbonized organic matter, plastic granules, other insoluble granules, soaps, ground microbiological, plant or animal matter. Such materials would cause a microgranulomatous response with collagen/fibroblast proliferation. Plastic or pressure resistant tubes or tubules on the order of 0.01 cm to 1 cm may transmit prolotherapy agents via the inert or insulated tubing to the prolotherapy emitting embodiment of the planar-tissue-altering-window/zone. Said tubules may terminate in small spray nozzles in other embodiments to allow spray distribution of prolotherapy agents onto the target surfaces. In the prolotherapy embodiment, prolotherapy agents or other tissue altering medicines are made ready in an IV bag or other reservoir located outside the shaft and gated nearby there. Gravitational progression of fluids from IV bags may be sufficient to distribute the prolotherapy agents through several meters of IV tubing through the shaft onto the "window/zone." For drip or spray distributions, the prolotherapy agent may be forced on its passage from the reservoir by numerous methods known in the art including but not limited to peristaltic pump, pressurized gas instillation, powered injection system and a pressurize-able reservoir. Flow rates and pressure rates may vary depending upon the concentration, volume, desired tissue contraction time and type of agent applied and may vary from 0.01 cc to 10 cc per minute. Footswitch control or voice activated control (in addition to optional thermal sensor/CPU feedback loops) of fluid release would allow convenience since the operating surgeon's hand may be occupied with device motion or activation of the lysing function of the device.

Planar-tissue-altering-window/zone embodiments for Uniform Heating Elements may be constructed by incorporating uniform tissue heating elements on one side of the proximal tip connected to an insulated conductive element passing through the shaft that are controllably electrified at handle in a fashion independent from the radiofrequency elements in the lysing segments. Thermal sensors nearby monitor tissue temperatures in order to create feedback or audible output to the surgeon or a computer so as to controllably apportion energy to the target tissues. This loop may thus controllably restrict thermal tissue damage and optimize contraction results. The thermal sensors may be of an infrared type, optical fiber type, an electronic type, or optical fluorescence type, each being known in the prior art and thus a detailed description thereof is deemed unnecessary.

Planar-tissue-altering-window/zone for a Thermal Energized embodiment allows thermal energy to escape from within the shaft where tip can be integral or a continuation of shaft made of similar metal or materials. The tip may also be constructed of materials that are both electrically non-conductive and of low thermal conductivity; such materials might be porcelain, ceramics or plastics. Portions of the tip and shaft may be covered with Teflon® to facilitate smooth movement of the device under the skin. A hot filament within the device is heated by flowing current through connecting wires and is held rigidly in position within a parabolic cavity by the strength of the wire. Alternately, the filament is fixedly attached to the shaft. The hot filament emits optical and thermal radiation that can directly exit the planar-tissue-altering-window/zone or be reflected off a reflector to also exit through window. The reflector can have a parabolic shape to effectively collect all optical and thermal radiation emitted away from the window. The hot filament can be a tungsten carbide filament similar to those used in high power light bulbs. The wavelength may be adjusted and controlled by adjusting the filament temperature/current. The window can be selected from a wide variety of glass that transmits optical, near infrared and infrared light (e.g., quartz, fused silica and germanium.) The tissue penetration depth depends on the wavelength of the light (e.g., 1 µm penetrates through 10 mm, 10 µm penetrates through 0.02 mm). The broad emission spectrum from the hot filament can be filtered to achieve the desired tissue effect. In particular filtering the emission spectrum to heat the dermis to temperatures of approximately 70° C. will cause the desired collagen shrinkage and tightening. The optimum spectral filtering depends on skin thickness and structure. A thermal sensors connected to the control unit by electrical wire monitors the temperature of tissue that is in contact with the shaft. In order to eliminate excessive heating of the shaft and the surrounding facial tissue, a heating element and reflector are thermally isolated by low thermal conductivity materials. The element is isolated by not touching the shaft, whereas the reflector can have an isolating layer where it attaches to the shaft. In addition, cold nitrogen gas can be injected through tube and pumped out through the hollow shaft to cool the tip and shaft. Flowing nitrogen gas (or another inert gas) through the hollow shaft also reduces oxidation damage to the filament. An alternative embodiment in co-pending applications places the hot filament in the handle while emitted optical and thermal radiation is reflected off a mirror through the window. An alternative embodiment in co-pending applications allows tissue heating is achieved by the direct contact with a hot surface where electric current flowing through wires heats a resistive load made of single or multiple elements to a user selected temperature. The resistive load could be a thin film resistor and the film temperature could be estimated from the measured resistance. Alternatively, separate thermal sensors placed close to the heating element measure temperatures which are sent to a control unit to control the current through the resistive load. Cold gas or liquid can be injected through tubes and pumped out through the shaft. Also, the heating element could be the hot side of a Peltier thermoelectric cooler which advantageously cools the opposite surface below ambient temperature with differences of up to 40° C. Thermal embodiments wherein heat is derived via magnetic or frictional methods may bring about similar tissue alterations.

In all embodiments of the device, the shaft can be coated with a biocompatible non-stick material such as Teflon® to reduce friction from tissue sticking to the device during the procedure.

The present invention can also create well-defined limited or isolated pockets in human tissue planes or locations for the implantation of organic or inorganic implants. For example, operation of Applicant and applicant's prior related art over a 'weak' cheekbone for an area mimicking the shape of the underlying cheekbone, and the additional desired look, yields a pocket into which the organic or inorganic implantable liquids or semisolids may be injected. Current implantable materials include but are not limited to: Absorbable suture material Polyglactic acid (Vicryl®, Polysorb®), Polyglycolic acid (Dexon®), Polydioxanone (PDS II®), Glycolic acid (Maxon®), Poliglecaprone 25 (Monocryl®), Glycoer 631 (Biosyn®), Surgical gut (plain), Surgical gut (chromic), Surgical gut (fast-absorbing). Nonabsorbable Suture material: Nylon (Ethilon®, Dermalon®, Nurulon®, Surgilon®)—braided or unbraided Polypropylene (Prolene®, Surgilene®, Surgipro®), Silk, Polyester (Dacron®, Mersilene®, Ethibond®), Polybutester (Novafil®), Surgical Stainless steel®. Grafts/Meshes including but not limited to: Expanded polytetrafluoroethylene (ePTFE) (Gore-Tex®, SoftForm®), Polyethylene (Dacron®), Polypropylene (Prolene®, Marlex®), Polyglactin (Vicryl®, Dexon®), Polyethylene terephthalate (Mersilene®), Polypropylene/polyglactin (Vypro®), Alloderm®, Sepramesh® (polypropylene mesh coated on one side with sodium hyaluronate and carboxymethylcellulose), Seprafilm® (sodium hyaluronate and carboxymethylcellulose), Silicone, PROCEED® Surgical Mesh, ULTRA-PRO® Partially Absorbable Lightweight Mesh Surgical Titanium Mesh®. Miscellaneous materials including but not limited to: Bovine collagen (Zyderm® collagen I, Zyderm® collagen II, Zyplast®), Human-derived collagen (Deramologen®, Cymetra®), Cadaveric fascia lata (Fascian®), Porcine collagen, Hyaluronic acid derivatives (Restylane®, Hylaform®, Hylan B® gel, Perlane®), Alloderm® (acellular allograft dermal matrix), Polyethylene terephthalate (Mersilene®), Proplast®, Medpor®, Titanium metal alloy, Vitallium metal alloy, Silicone, Hydroxyapatite, Bioglass, and Nonceramic hydroxyapatite.

For decades plastic surgeons have inserted biological and non-biological, organic and inorganic meshes into the face to remedy defects and lend support, and other areas such as the abdomen and groin to lend support and to hold back herniated tissues. However, placement of the meshes necessitated much larger surgical openings than would be necessary with applicant and co-pending which are uniquely. able to allow large potential free surface areas for mesh to be implanted upon while fitting such large meshes through only minimally invasive incisions. Meshes can be made of: body-reactive organic substances including cotton and silk; body-inert organic substances such as plastics, polypropylene or Gore-Tex® (low density polyethylene); materials in-between, for example, nylon is minimally reactive; inorganic substances such as stainless steel or other metals and silicone. Meshes can be unfolded or unrolled after insertion through the minimally invasive entrance wounds to occupy any or all of the tissue planes that were separated. Meshes can be fashioned to extend in the upper neck to extend almost from earlobe to earlobe to act as a sling when stitch secured into place. On the other hand, mesh fixation can be delayed or allowed to heal (or fibrose=collagen form) into place over several months before reopening small portions of the tissue planes containing the supportive mesh for vectored stitch tightening. Deposited meshes can be sewn immediately to create tension and/or support. Location and proper unraveling of meshes can be determined by endoscope or by portable x-ray via radio-opaque paint or lacing with metals or elements or compounds. Meshes can be made "stickier" to incoming collagen and fibrous tissues by sandblasting, rasping or chemically altering the material prior to sterilization. The surgical device can also be used to deposit well-defined implants such as "cheekbone" type in a minimally invasive manner or fluid, semisolid or other implants with less definitions. Depending upon the need for suspension of lax or prolapsed tissues, nets, meshes or slings of biologically compatible organic or inorganic materials such as the following may be implanted for immediate suture fixation or tightening. Alternatively, biocompatible materials may be allowed to "heal in place" so as to strengthen the underlying tissues for a later or delayed surgical procedure. The following list of potential implantable bioabsorbable and nonabsorbable materials is not exhaustive and not intended to be limiting: polyglactic acid, polyglycolic acid, polydioxanone, glycolic acid, poliglecaprone 25, glycoer 631, nylon, polypropylene, silk, cotton, polyester, polybutester, surgical Stainless steel, expanded polytetrafluoroethylene (ePTFE), polyethylene, polyglactin, polyethylene, terephthalate, Dacron®, Alloderm®, Sepramesh® (polypropylene mesh coated on one side with sodium hyaluronate and carboxymethylcellulose), Seprafilm® (sodium hyaluronate and carboxymethylcellulose), silicone, PROCEED® Surgical Mesh, ULTRAPRO® Partially Absorbable Lightweight Mesh, Surgical Titanium Mesh®, bovine or human or porcine-derived collagen, cadaveric fascia lata (Fascian®), hyaluronic acid derivatives, Alloderm® (acellular allograft dermal matrix), polyethylene terephthalate (Mersilene®), Proplast®, Medpor®, titanium metal alloy, vitallium metal alloy, hydroxyapatite, bioglass, and nonceramic hydroxyapatite. For example, a Gore-tex® sling may be strung through minimal incisions into the large underlying lysed plane using typical surgical instrumentation such as forceps, hooks, clamps and malleable guide-wires between the fibrous tissues and under the neck from the right to the left mastoid regions if the incisions are located in the infraauricular regions. Meshes may be unrolled once fed into the lysed facial planes through the minimal incision sites and maneuvered into place via probes or instruments placed in any of the incision sites; proper seating of the mesh may be detected endoscopically, fiberoptically, and ultrasonographically. If metal tags such as metallic thread are laced intermittently to the edge of the mesh then radiological evaluation is possible especially if the mesh is itself is comprised of, or attached to, any radio-opaque biocompatible material. Meshes on small <2 cm wide but <1 cm thick rollers fitted with a loose <6 cm wire or monofilamentous plastic loops passing through the center of the "roller" may be fed into incision sites and received with, a probe, instrument or malleable hook to unroll the mesh in varying directions using other incision sites. Alternatively, the device may be used in a more limited fashion to create precise, isolated, uniform tissue pockets at tissue plane levels chosen by the surgeon over such areas such as the malar eminences (cheekbones) so standard implants may be fed through the device entrance incisions, with some scalpel expansion of the entrance wounds or from some other location, for example, intraoral. Precise pockets may be created to receive biocompatible thermosetting or time setting or reactant setting soft foam that is restricted to the shape of the instrument-created pocket and can be finger sculpted or template sculpted by applying pressure during setting. Following any of the above measures, two absorbable buried 5-0 Monocryl® (Ethicon division of Johnson & Johnson, Piscataway, N.J.) stitches are placed in each incision. A dressing is usually not needed and the patient may return to work or relax at home. Alternatively, if significant prolotherapy or implantable material is placed a loose floss-filament dressing may be applied around the face for 24 to 48 hours. If the patient is prone to swelling or bleeding, a small Jackson-Pratt drain may be placed through any incision site and sutured into place underneath the dressing.

Planning obsolescence is integral to maintaining proper performance and quality of a device over time. Interposed among, along or between segments of either the circuitry and/or the fiberoptics of the aforementioned embodiments may be hardware or software on for example a card or a chip. The card or chip or other usage monitoring subdevice may be inserted into a receiving area in such a place as the handle or adjacent the electrosurgical generator; it can either record data including but not limited to time usage of, cutting current, coagulation current or blend value. The subdevice, interposed into the circuitry, fiberoptics or other energy delivery mechanisms can terminate the functions of the device unless some type of criteria is met for reactivation. Criteria might be obtaining a password, new card or chip following a payment. This and other plans for metered, monitored or restricted usage that are currently known in the art may be used in conjunction with embodiments presented.

Operative Procedure: Following informed consent and having been free of eating or drinking for 12 hours, the patient is placed in the supine position. The face and neck are cleansed with standard preoperative cleansers such as iodine or chlorhexidine. Minimal incision sites of 1 cm are marked at any position along the preauricular or infraauricular line at the surgeon's discretion. Further 1 cm minimal incision sites are marked with a surgical marker in areas that may include the submental (below the chin) zone in order to reach the neck and possibly in the superiormost forehead within the hairline in order to disguise the incision. The small zones of skin overlying the regions where the motor nerves at risk (marginal mandibular nerve, frontal branch of the facial nerve, spinal accessory nerve) are demarcated with dashed lines of surgical marker. By this point, the patient has chosen the option of being twilight-sedated intravenously or given general anesthesia by endotracheal tube or LMA (laryngeal mask airway) although most patients do not require any of these measures to endure the remainder of the procedure. The surgically marked incision sites are further cleansed and then injected with only 1 cc of 1% lidocaine with 1:100,000 epinephrine each and allowed to settle for 3 minutes. Each area is incised with a #15 scalpel blade through the epidermis and dermis into the subcutaneous layer; the forehead site should be incised parallel to the hair follicles to prevent baldness in the area. 1 liter of Klein tumescent solution is prepared with the following recipe: 1 liter of normal saline into which is mixed, 40 cc of 2% lidocaine and 10 cc of 10 mEq/L of $NaHCO_3$ and 1:1,000 epinephrine. Only 50 cc to 200 cc of the Klein tumescent solution is rapidly peristaltically pumped into areas reachable by each incision site into the subcutaneous layer using a spinal needle or a 2 mm wedge-tipped or spatula-tipped fluid instillation catheter in a fanning motion similar to the vectors which will ultimately be the directions of later passage for the facial tightening device. After the few minutes needed for Klein tumescent instillation, the Klein solution is allowed to settle for 15 minutes for maximum effect. One of the selected device embodiments described herein is maintained sterile and is attached to one or more electrosurgical generators or lasers or other energy form generators. Prior to using an electrosurgical window/zone embodiment, set the electrosurgical generator to the appropriate cut and coagulation settings. The chosen device is inserted into one the incision sites while being held firmly at the handle and pushed forcefully axially while lifting occurs. Motion, while the device is activated by footswitch or handle rocker or activating button, is commenced along straight lines radiating from the incision sites in a spoke-wheel fashion as far as possible usually without entering the eyelid region or the lips or the demarcated zones of superficial motor nerves. Depending upon the quality of tissue being lysed, patient age, prior facial surgery history, medical history, physical examination, patient demographics, the tissue planar-tissue-altering-window/zone may be activated "face up" to energize the dermis or "face down" to energize the subcutaneous which will leak fatty acids and draw inflammatory cells and mediators which in turn stimulate the opposing dermal layer fibroblasts to manufacture collagen; a combination of "face up" and "face down" can also be used. Traumatizing the underlying subcutaneous tissue or "cooking the fat," causes inflammation in the subcutaneous layer which transfers to over-draping dermal flap causing dermal inflammation and thus contraction (unpublished, preparing manuscript to be submitted to medical journal). Likewise, traumatizing underlying muscle (in this case the platysma muscle that envelopes most of the front of the neck) to cause char or other debris, may cause a similar contractile response in the platysma and the over-draping dermal skin flap. The formation of carbon and carbonized organic chemicals (matter) likely induces inflammation via several pathways including: bringing macrophages which have to envelope and digest the material and by inducing leakage of cellular mediators which inflammatory cell gatherings and their resultant tissue cascade and tissue modifications. Additionally, energy application from the planar-tissue-altering-window/zone may occur on withdrawal portion of the stroke as opposed to the thrust portion. The thrust portion may or may not provide the most cool environment to the window/zone which may vary with the energy level associated with the electrosurgical tissue lysing element. External cooling devices may be applied to the facial skin before, during or after treatment, for example, ice cool water soaked towels or ice cold water circulated through a externally conforming bag to enhance the reverse thermal gradient. Depending upon numerous factors including the energy type and amount used, additional lysed tissue plane modification may be needed using prolotherapy solutions which may be injected via canals contained in or along the shaft or by a separate catheter mechanism. Such a solution as 250 cc of 25% NaCl (hypertonic saline) may be instilled into the freshly cleaved facial interplane space following activated instrument passage, massaged or allowed to sit for 10 minutes and then pressed out through the incision sites and then neutralized with 2 flushes of normal saline instilled in a separate catheter system, which instilled the tumescent solution, which is then pressed out through the same incision sites. Prolotherapy agents known in the art to enhance tissue fibrosis and collagenization of the human joints include scierosing or proliferative solutions such as hypertonic glucose (D-glucose), sodium morrhuate, and phenol. Fibrosis-inducing chemicals or mixtures in liquid, foam, suspension, powder, or any other form known to possess the ability to stimulate fibroblasts or increase collagenization (including but not limited to sodium deoxycholate, polidocanol, sodium docecyl sulfate) may be instilled similarly to the previously described 25% NaCl. If acids or bases are used to deliberately traumatize tissue to induce fibrosis then they may be neutralized by their opposing party for example an acid solution induces trauma and is neutralized by a dilute sodium bicarbonate lavage.

A potential benefit of beard and neck region of using either the passage of the energized relative recession or the tissue-altering-window/zone is that hair loss will occur with standard settings in males, because the design uniquely places the cutting segment at the lower level of the hair bulbs which causes destruction of the hair bulb. Regrowth is usually impeded following said trauma.

The foregoing description of preferred embodiments and methods of use of the invention are presented for purposes of illustration and description and are not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

I claim:

1. An apparatus, comprising:
    a shaft having a proximal end and a distal end;
    at least one recessed region positioned at said distal end, each of said at least one recessed region including means for delivering energy to separate tissue; and
    an array of energy delivery elements for delivering energy to at least two tissue locations, wherein said array of energy delivery elements for delivering energy is positioned and configured on said shaft so as to deliver energy to a surface of tissue created by separating said tissue with said at least one recessed region, and wherein said array of energy delivery elements is configured to alter tissue at each tissue location of said at least two tissue locations with less relative tissue alteration between each said tissue location.

2. The apparatus of claim 1, wherein said energy delivery elements deliver G at least one of electrical energy, thermal energy, and electromagnetic energy.

3. The apparatus of claim 2, wherein said electrical energy comprises at least one of monopolar electrical current and bipolar electrical current.

4. The apparatus of claim 1, wherein said means delivers radiofrequency electrosurgical current.

5. The apparatus of claim 1, wherein said energy delivery elements deliver chemical energy.

6. The apparatus of claim 5, wherein said chemical energy comprises an acid.

7. The apparatus of claim 5, wherein said chemical energy is derived from at least one material selected from the group consisting of a prolotherapy chemical, sugar, a salt solution, a detergent, and an acid.

8. The apparatus of claim 5, wherein said chemical energy is derived from at least one material selected from the group consisting of hypertonic glucose (D-glucose), sodium morrhuate, phenol, hypertonic saline, sodium deoxycholate, polidocanol, sodium docecyl sulfate, trichloroacetic acid, and glycolic acid.

9. The apparatus of claim 5, wherein said chemical energy is derived from at least one material selected from the group consisting of a tissue-inflammation inducing chemical, a tissue-traumatizing chemical, a fibrosis-inducing chemical, a suspension, an insoluble granule, soap, microbiological matter, plant matter, animal matter, gas, liquid and fibroblast growth inducing matter, a fat, a base, an oil, collagen, sand, glass, and plastic.

10. The apparatus of claim 1, wherein each of said at least one recessed region comprises means for lysing tissue.

11. The apparatus of claim 10, wherein said means for lysing tissue comprises means for providing lysing energy.

12. The apparatus of claim 11, wherein said lysing energy comprises at least one of electrical energy, and electromagnetic energy.

13. The apparatus of claim 11, wherein said lysing energy comprises ultrasound energy.

14. The apparatus of claim 1, wherein each of said at least one recessed region comprises to a lysing segment, and further comprising means for providing energy to each of the lysing segments.

15. The apparatus of claim 14, wherein said energy for said lysing segment comprises electromagnetic energy.

16. The apparatus of claim 14, wherein said energy for said lysing segment comprises radiofrequency electrosurgical current.

17. The apparatus of claim 1, wherein said array of energy delivery elements damages tissue at each tissue location of said at least two tissue locations without damaging tissue between each said tissue location.

18. The apparatus of claim 1, further comprising a least one inductance sensor attached to said shaft that senses tissue inductance around said distal end of said shaft, wherein said sensor sends a signal to control means, and wherein said control means controls the delivery of said energy to said distal end to modulate said inductance.

19. The apparatus of claim 1, wherein said array of energy delivery elements comprises a plurality of electrodes.

20. The apparatus of claim 19, wherein at least one electrode of said plurality of electrodes comprises an insulated portion.

21. The apparatus of claim 19, wherein at least one electrode of said plurality of electrodes comprises at least one shape selected from the group consisting of a pointed cone with its larger diameter base embedded or counter-sunk in said shaft, a cube, a pyramid, a hemisphere, a sphere with a cylindrical attachment area, a non-pointed cylinder, a bristle, and a branched bristle.

22. The apparatus of claim 19, wherein said plurality of electrodes comprises at least four electrodes and no more than fifty electrodes.

23. The apparatus of claim 1, wherein said array of energy delivery elements comprises means for limiting the number of times said apparatus can be used.

24. The apparatus of claim 1, wherein said array of energy delivery elements comprises a dome covered with insulation containing at least two holes, wherein each hole of said at least two holes is configured to transmit energy.

25. The apparatus of claim 1, wherein said array of energy delivery elements comprises means for providing gated energy.

26. The apparatus of claim 25, wherein said gated energy is gated at a rate within a range from 1 Hz to 200 Hz.

27. The apparatus of claim 1, further comprising means for providing cryogenic material, wherein the means for providing cryogenic material is connected with said shaft.

28. The apparatus of claim 1, further comprising means for limiting the number of times said apparatus can be used.

29. The apparatus of claim 1, wherein said energy delivery elements deliver ultrasound energy.

30. An apparatus for performing a face-lifting medical procedure, comprising:
a shaft having a proximal end and a distal end;
a plurality of protruding members positioned at said distal end; and
a recessed region positioned at said distal end between each of said protruding members, each of said recessed regions including means for delivering energy to separate tissue along said distal end.

31. The apparatus of claim 30, wherein said energy comprises at least one of laser energy, radiofrequency electrosurgical current, and electromagnetic energy.

32. The apparatus of claim 30, wherein said shaft comprises a first substantially planar surface and a second substantially planar surface, wherein the first substantially planar surface is opposite from the second substantially planar surface.

33. The apparatus of claim 30, wherein said protruding members comprise bulbous protruding members.

34. The apparatus of claim 30, further comprising an energy delivery area positioned on said shaft for delivering energy to a surface of tissue created by separating said tissue into tissue planes.

35. The apparatus of claim 34, wherein said energy delivery area delivers at least one of electrical energy, thermal energy, electromagnetic energy, and chemical energy.

36. The apparatus of claim 34, wherein said energy delivery area comprises an array of individual energy delivery elements.

37. The apparatus of claim 36, wherein said array of energy delivery elements alters tissue at each of a plurality of tissue locations with less relative tissue alteration between each said tissue location.

38. The apparatus of claim 34, wherein said energy delivery area delivers is configured to deliver ultrasound energy.

39. The apparatus of claim 30, wherein said shaft comprises a plurality of recessed regions at said distal end.

40. The apparatus of claim 30, wherein said energy comprises ultrasound energy.

* * * * *